(12) United States Patent
Giudiceandrea et al.

(10) Patent No.: US 8,780,360 B2
(45) Date of Patent: Jul. 15, 2014

(54) METHOD AND APPARATUS FOR IDENTIFYING THE ORIENTATION OF WOOD FIBRES

(75) Inventors: Federico Giudiceandrea, Bressanone (IT); Peter Matthews, Poole (GB)

(73) Assignee: Microtec S.R.L., Bressanone (IT)

( * ) Notice: Subject to any disclaimer, the term of this patent is extended or adjusted under 35 U.S.C. 154(b) by 235 days.

(21) Appl. No.: 13/383,782

(22) PCT Filed: Jul. 15, 2009

(86) PCT No.: PCT/IT2009/000308
§ 371 (c)(1),
(2), (4) Date: Mar. 9, 2012

(87) PCT Pub. No.: WO2011/007374
PCT Pub. Date: Jan. 20, 2011

(65) Prior Publication Data
US 2012/0170055 A1    Jul. 5, 2012

(51) Int. Cl.
*G01B 11/14*    (2006.01)
(52) U.S. Cl.
USPC .......................................................... 356/614
(58) Field of Classification Search
CPC ...................................................... G01B 11/14
USPC .......................................................... 356/614
See application file for complete search history.

(56) References Cited

U.S. PATENT DOCUMENTS

| T932,008 I4 | 3/1975 | Davis et al. |
| 3,976,384 A | 8/1976 | Matthews et al. |

(Continued)

FOREIGN PATENT DOCUMENTS

| DE | 195 47 553 C1 | 3/1997 |
| EP | 1 193 469 A1 | 4/2002 |

(Continued)

OTHER PUBLICATIONS

Shen J. et al., "Optical Scattering Polarization Measurements of Fiber Orientation of Wood with Rough Surfaces", Proc. of SPIE: Optical Engineering for Sensing and Nanotechnology (ICOSN 2001), vol. 4416, 2001, pp. 31-34, XP002580214.

*Primary Examiner* — Tarifur Chowdhury
*Assistant Examiner* — Omar Nixon
(74) *Attorney, Agent, or Firm* — Pearne & Gordon LLP

(57) ABSTRACT

A method for identifying the orientation of wood fibres (2) comprises the operating steps of generating at least one beam of light (4) polarised in a predetermined first polarisation plane, projecting the beam of light (4) onto a surface of a piece of wood (3) to illuminate a zone of said surface and generate diffuse light without polarisation and reflected light (5) polarised in a second polarisation plane (pX2), detecting the linearly polarised reflected light (5) and identifying the orientation of the illuminated fibres (2) at least indirectly based on the orientation in space of the second polarisation plane (pX2) of the reflected light (5). Also claimed is an apparatus (1) for implementing the method, comprising means for supporting a piece of wood (3), a light source (10) for generating at least one beam of light (4) polarised in a first polarisation plane (pS), a detection device (6) for detecting, in practice, the light coming from a zone of the piece of wood (3) illuminated by the beam of light (4) and for filtering said light based on its polarisation, and a processing device operatively connected at least to the detection device (6) for processing what is detected and identifying the orientation of the wood fibres (2) at the illuminated zone.

21 Claims, 16 Drawing Sheets

(56) References Cited

U.S. PATENT DOCUMENTS

| | | | |
|---|---|---|---|
| 4,482,250 A | 11/1984 | Hirvonen et al. | |
| 4,606,645 A | 8/1986 | Matthews et al. | |
| 4,764,017 A * | 8/1988 | Hirvonen | 356/369 |
| 5,252,836 A | 10/1993 | Matthews et al. | |
| 6,354,725 B1 * | 3/2002 | Simon | 362/576 |
| 6,624,883 B1 | 9/2003 | Zhou et al. | |
| 2002/0025061 A1 | 2/2002 | Metcalfe et al. | |
| 2003/0156286 A1 | 8/2003 | Takagi et al. | |
| 2005/0007591 A1 | 1/2005 | Shribak et al. | |
| 2005/0270529 A1 | 12/2005 | Yamagaki et al. | |
| 2009/0101297 A1 | 4/2009 | Jez et al. | |
| 2009/0273784 A1 | 11/2009 | Yamagaki et al. | |

FOREIGN PATENT DOCUMENTS

| | | |
|---|---|---|
| FR | 2 499 717 A1 | 8/1982 |
| GB | 2 285 861 A | 7/1995 |

* cited by examiner

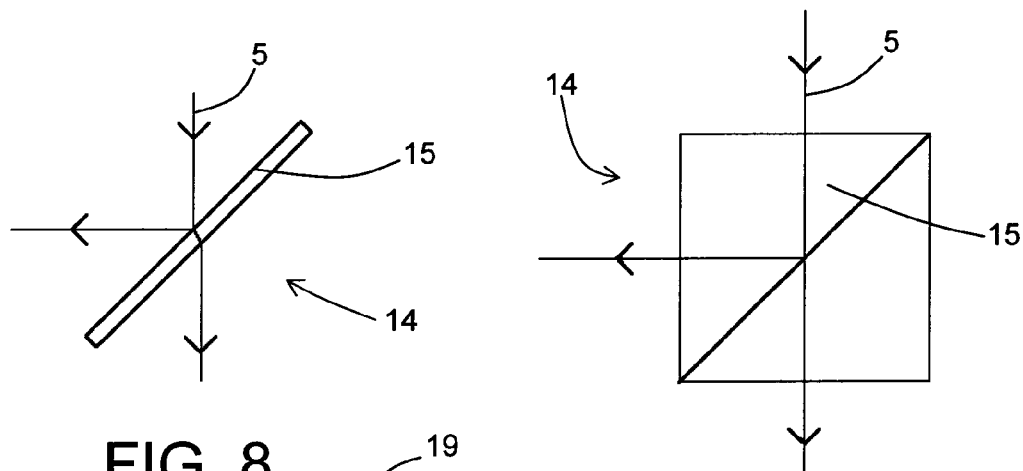
FIG. 8
FIG. 9
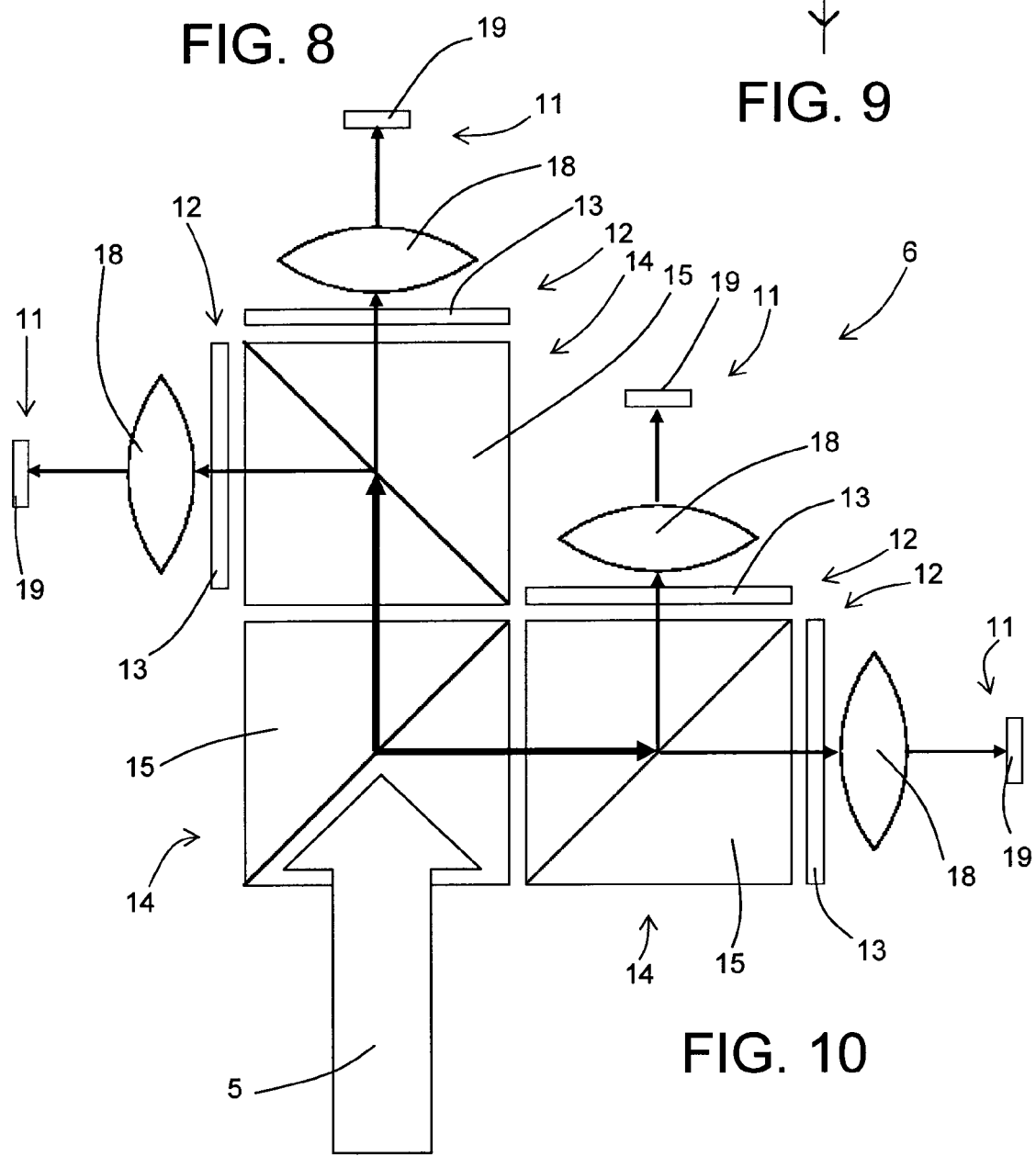
FIG. 10

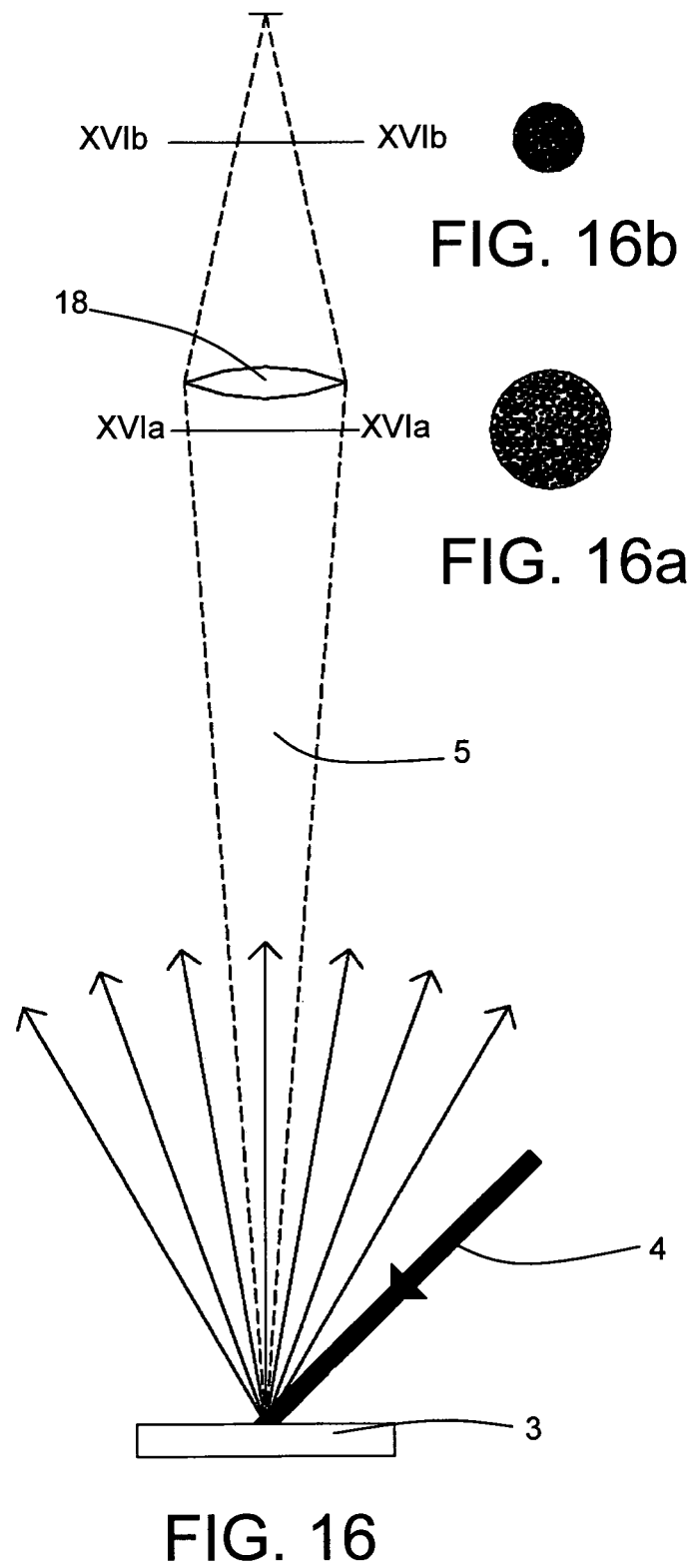

METHOD AND APPARATUS FOR IDENTIFYING THE ORIENTATION OF WOOD FIBRES

The present invention relates to a method and an apparatus for identifying the orientation of wood fibres, and therefore for measuring the angle formed by the fibres relative to a nominal reference direction.

Wood is a highly anisotropic material made up of bundles of various types of lignocellulosic fibres. Most of these fibres usually extend parallel with the pith or the longitudinal axis of the tree. However, growth abnormalities may greatly distort this parallelism in localised areas. One of these abnormalities is torsion. This is a situation in which the growing tree arranges the fibres in a spiral around the pith. A better known abnormality is knots. A knot is created when a growing tree forms new wood around an existing living or dead branch. Another example is the wounds affecting the cambium tissue below the bark. These wounds lead the growing tree to form a kind of scar tissue in which the direction of the fibres may vary in an uncontrolled way. The orientation of the fibres more commonly known as the direction of the grain, has a significant effect on the appearance and strength of the wood. Variations in the angle of the fibres are particularly important in wood intended for structural use or for constructions. For many uses in which tensions tend to cause bending, the load allowed is directly dependent on the uniformity and linearity of the orientation of the fibres in the wooden element. Ideally, in wood for constructions, all of the fibres should be parallel with the longest axis of the wooden element. This ideal condition is only approached in the highest quality timber, which is substantially free of defects such as knots. In any case, the probable presence of defects of the type that are less easy to see, such as those which may be caused by spiral fibres, means that timber quality classification is always carried out very carefully.

In light of such problems, over the years the need to have available apparatuses able to reliably and automatically identify the direction of wood fibre 2 has become increasingly urgent. The first examples of apparatuses relating to automatic evaluation of timber are described in U.S. Pat. No. 3,976,384 (by this inventor), FR 2,499,717 and US T 932,008.

A subsequent development is described in U.S. Pat. No. 4,606,645, also by this inventor, which describes a method for measuring the angle of wood fibres based on the intensity of light reflected by the wood in the various planes passing through the point illuminated. In said patent, the direction of the fibre 2 was assumed to be normal to the plane in which the intensity of the reflected light was at its maximum.

Further developments based on various principles are described in U.S. Pat. No. 5,252,836, again by this inventor, and US 2002/025061.

Another technology is described in U.S. Pat. No. 6,624,883. In this case the surface of the wood is illuminated with a beam of light polarised in a predetermined plane. Following said illumination it is assumed that spreading from the illuminated zone there is an elliptically polarised emergent light and a linearly polarised reflected light. Information about the orientation of the grain is obtained by processing the signal detected relative to the elliptically polarised emergent light.

Finally, patent GB 2 285 861 by this inventor establishes a link between the presence of grain defects and the polarisation of light reflected by a piece of wood.

Although up to now many solutions have been proposed for automatically identifying the direction of the grain in wood, based on principles which differ greatly, none of those solutions has yet proved capable of identifying the direction of the grain in a way that is precise and reliable enough.

In particular, none of said solutions has yet proved capable of identifying in a sufficiently precise and reliable way the direction of the grain not just parallel with the surface of the wood, but also in a direction incident on said surface ("diving grain").

Therefore, in this situation, the technical purpose which forms the basis of this invention is to provide a method and an apparatus for identifying the orientation of wood fibres which overcomes the above-mentioned disadvantages.

In particular, the technical purpose of this invention is to provide a method and an apparatus for identifying the orientation of wood fibres which allows precise evaluation of the orientation of the wood fibres first in the plane identified by the surface of the wood.

Secondly, the technical purpose of this invention is to provide a method and an apparatus for identifying the orientation of wood fibres even according to directions incident on the surface of the wood.

The technical purpose specified and the aims indicated are substantially achieved by a method and an apparatus for identifying the orientation of is wood fibres as described in the appended claims.

Further features and the advantages of the present invention are more apparent in the detailed description, with reference to the accompanying drawings which illustrate several preferred, non-limiting embodiments of a method and an apparatus for identifying the orientation of wood fibres, in which:

FIG. 8 shows a first example of a splitter for a beam of light used in the present invention;

FIG. 9 shows a second example of a splitter for a beam of light used in the present invention;

FIG. 10 is a schematic view of a detail of a first apparatus made according to the present invention;

Figure 17:
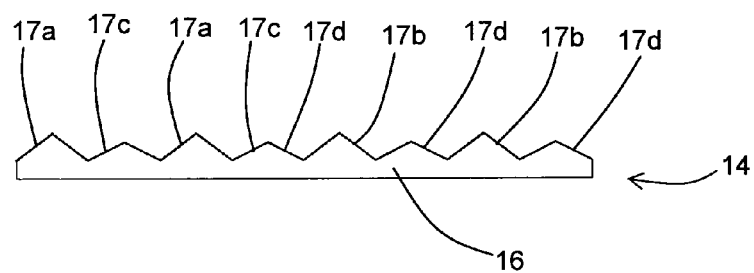
Figure 18:
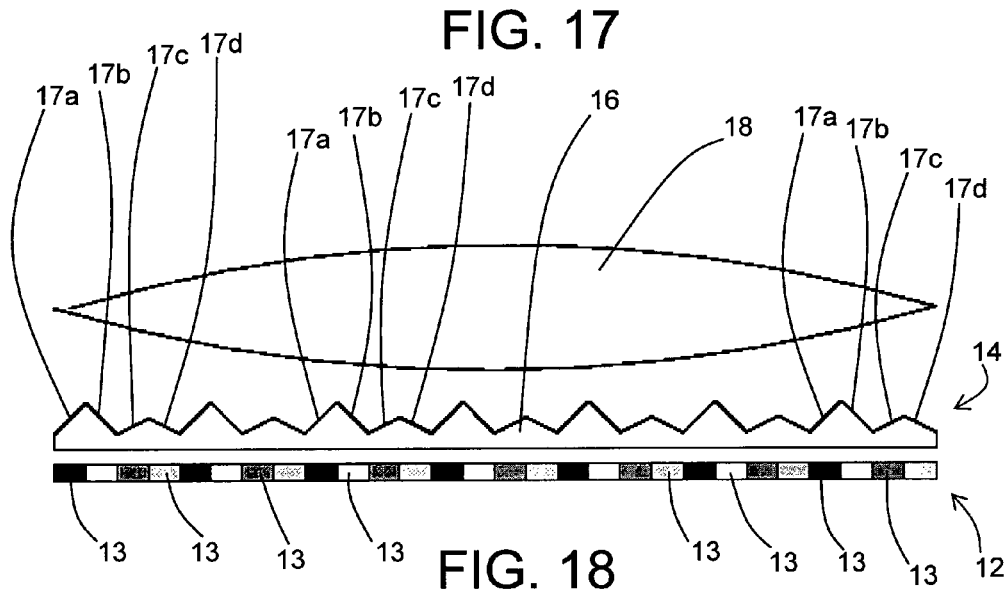

FIGS. 16, 16*a* (cross-section according to line XVIa-XVIa of FIGS. 16) and 16*b* (cross-section according to line XVIb-XVIb of FIG. 16) highlight a problem which may arise relative to implementation of the present invention;

FIG. 17 shows another example of a splitter for a beam of light designed to overcome the problem highlighted in FIG. 16; and FIG. 18 shows a detail of a possible embodiment of an apparatus incorporating a splitter like that of FIG. 17.

Figure 4:
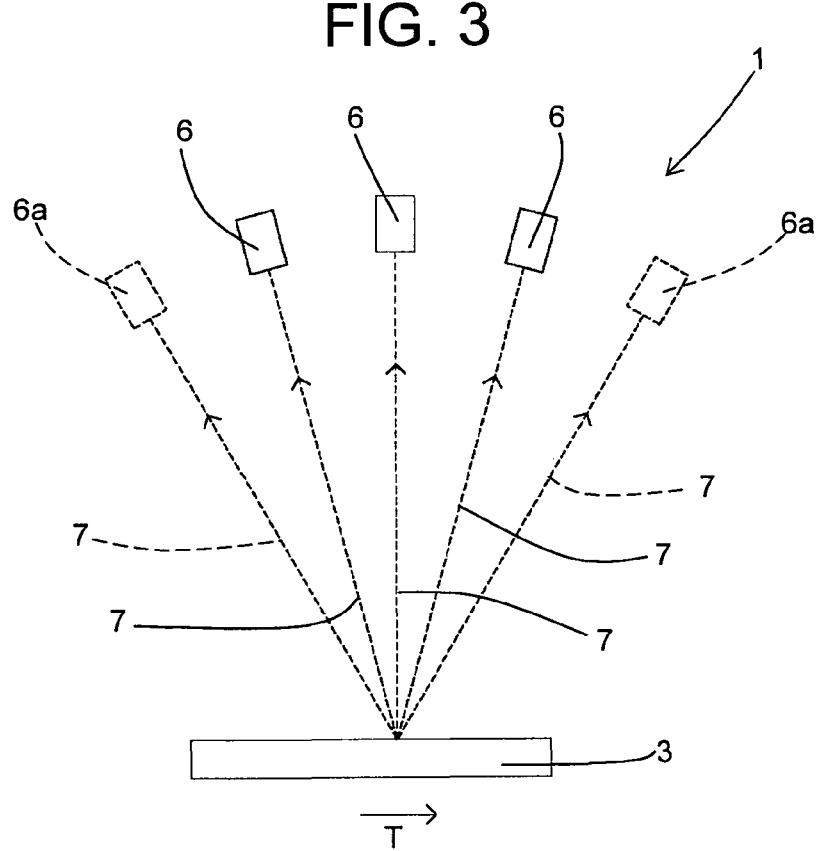
FIG. 4 is a schematic side view of an apparatus made according to the present invention.
Figure 19:
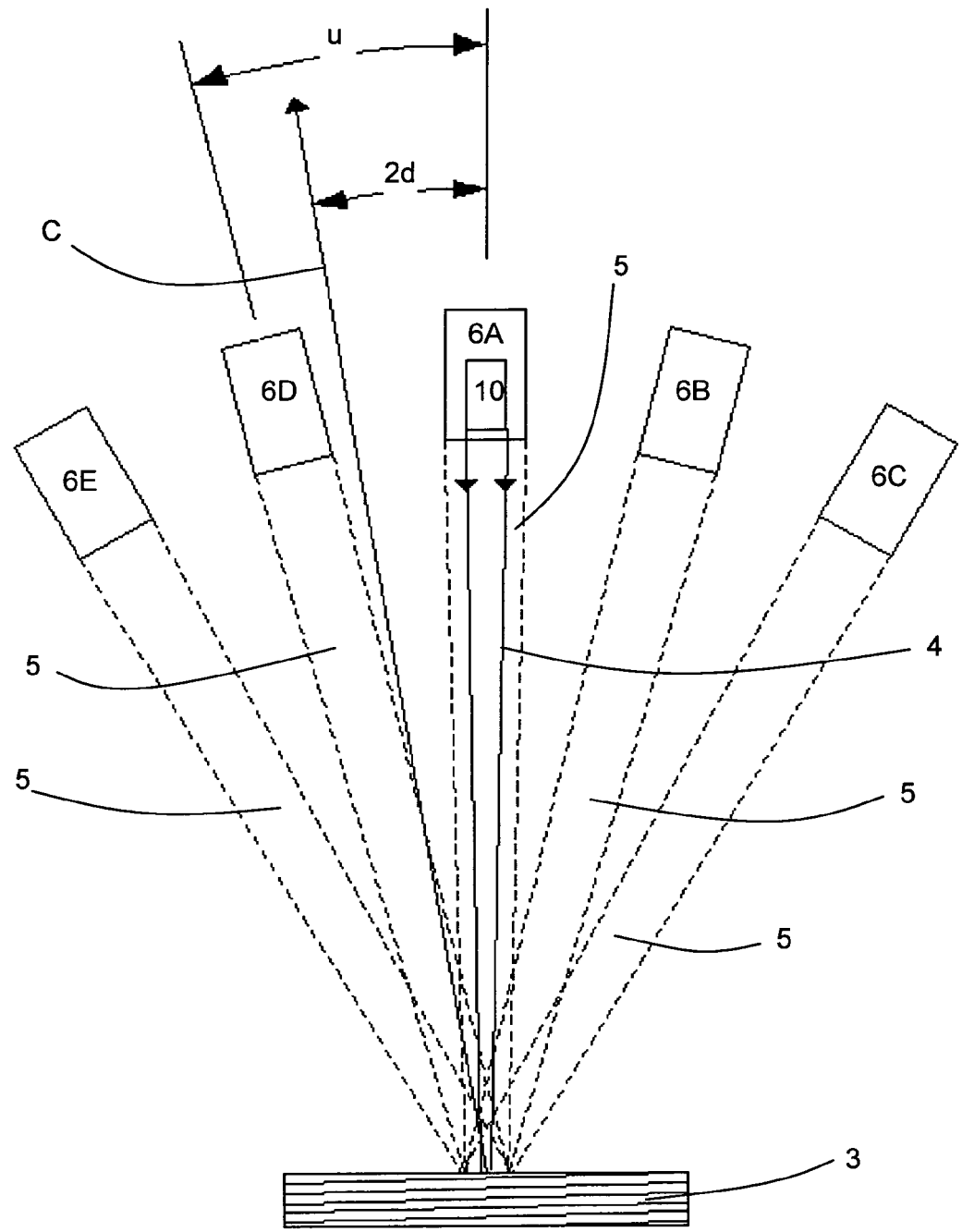
Figure 20:
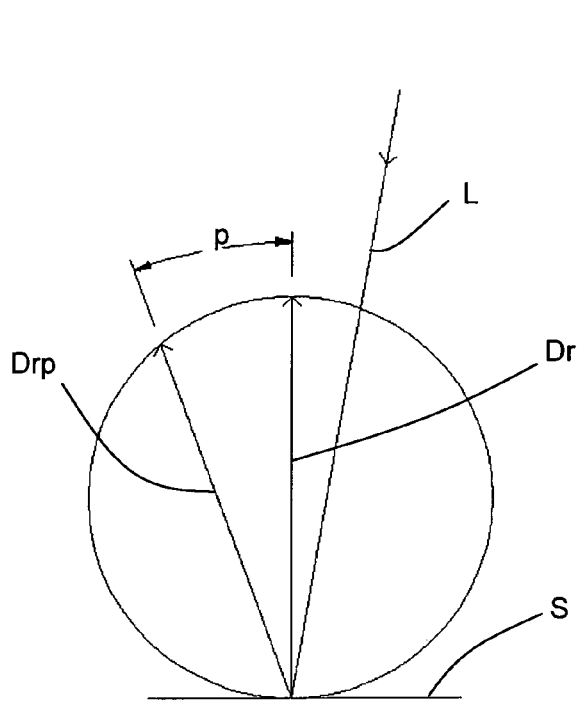
Figure 22:
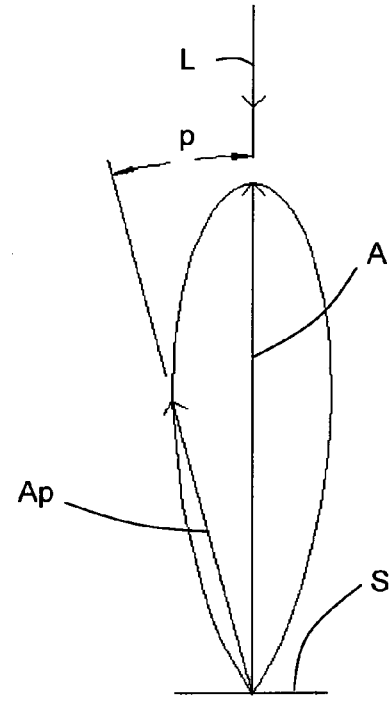
Figure 24:
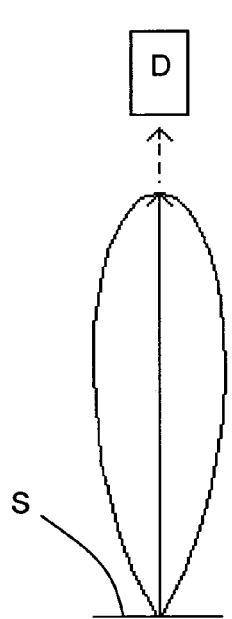
Figure 25:
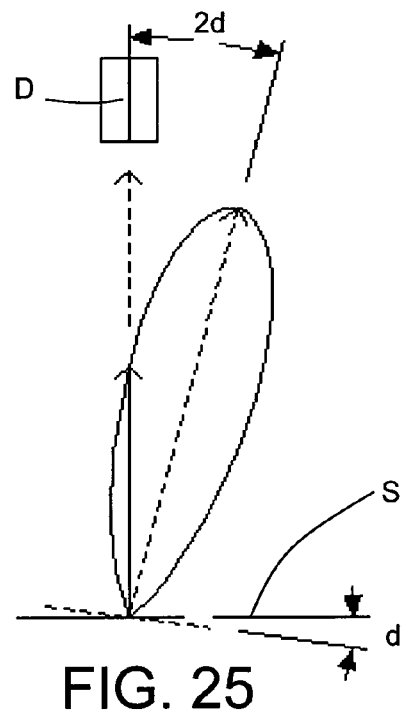
Figure 21:
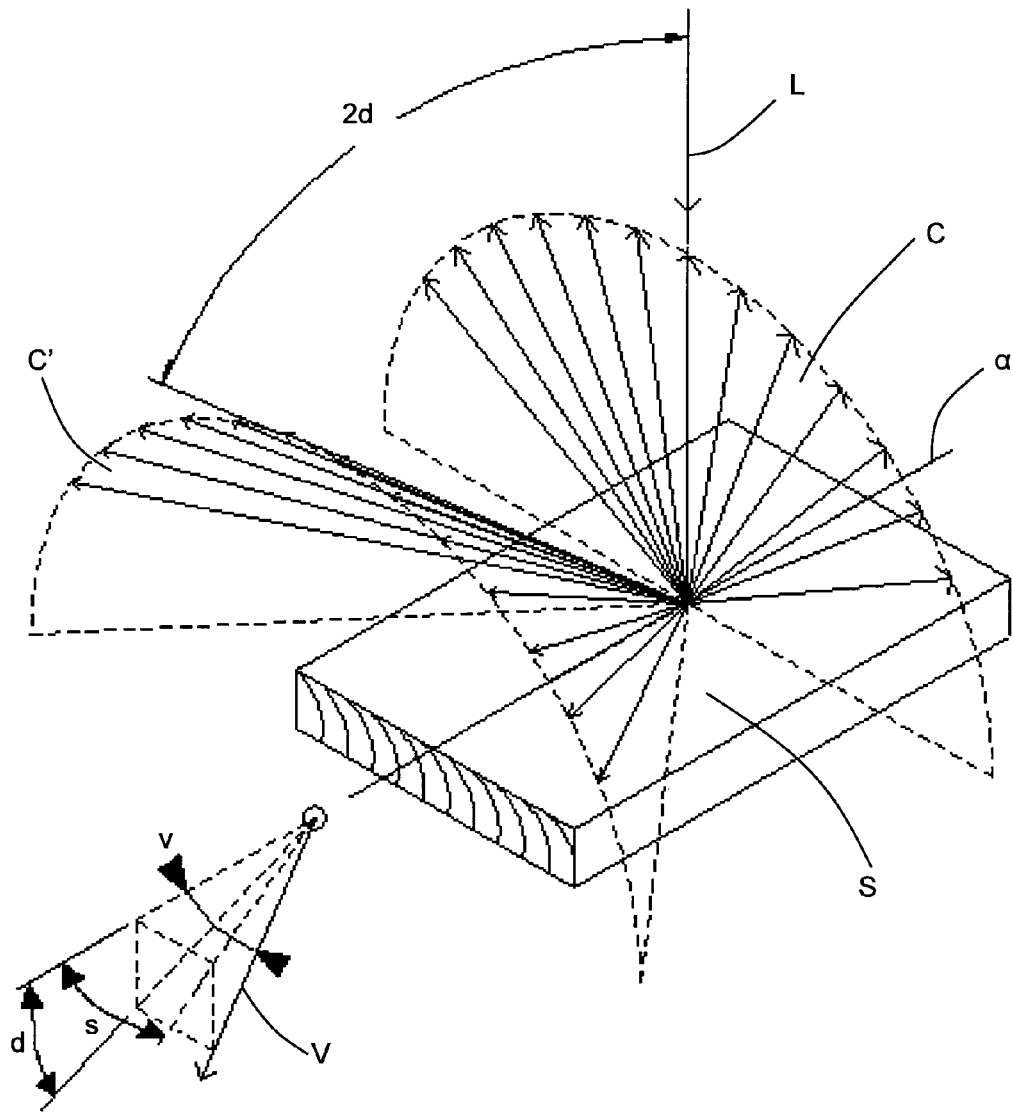
Figure 23:
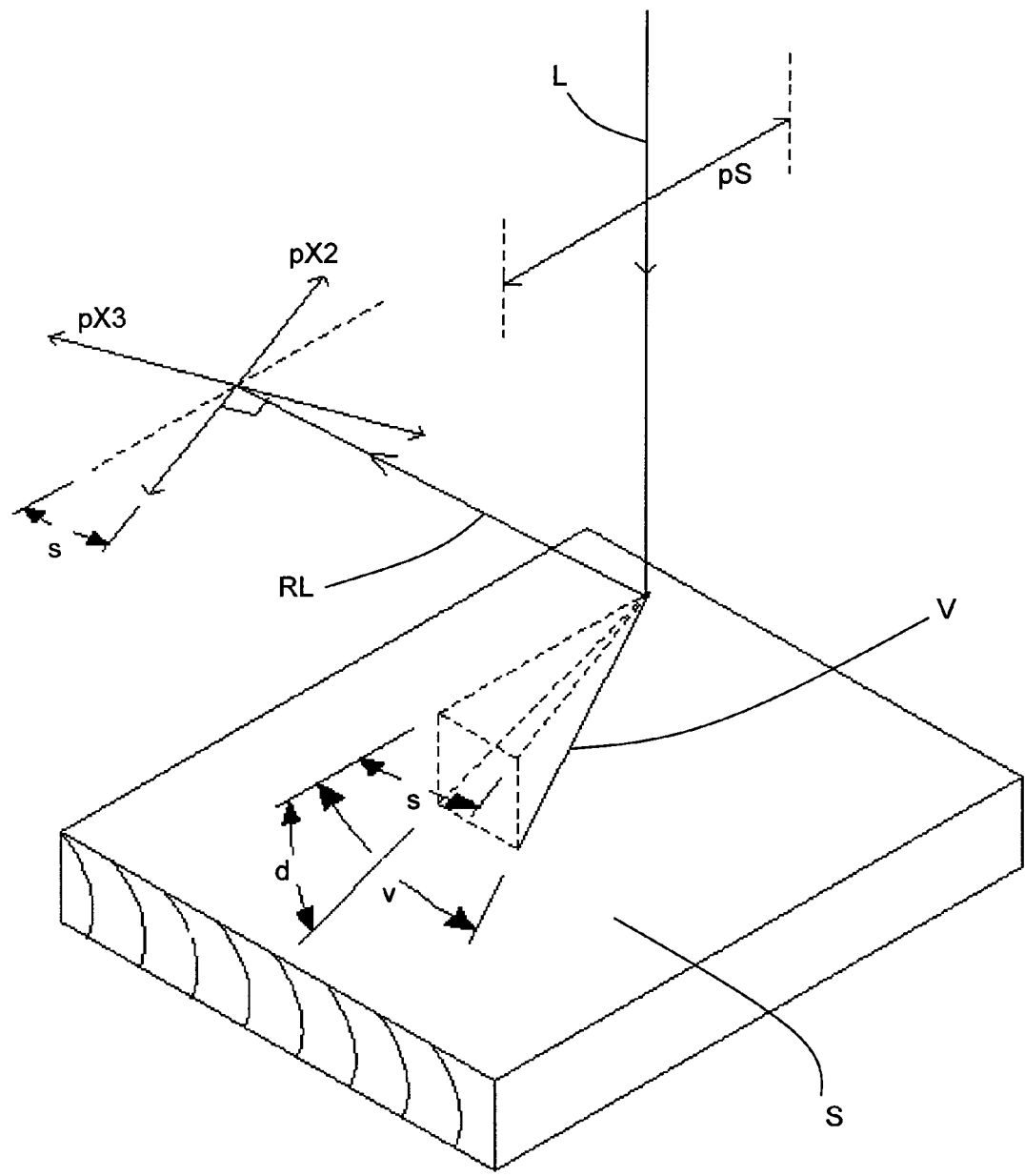
Figure 26:
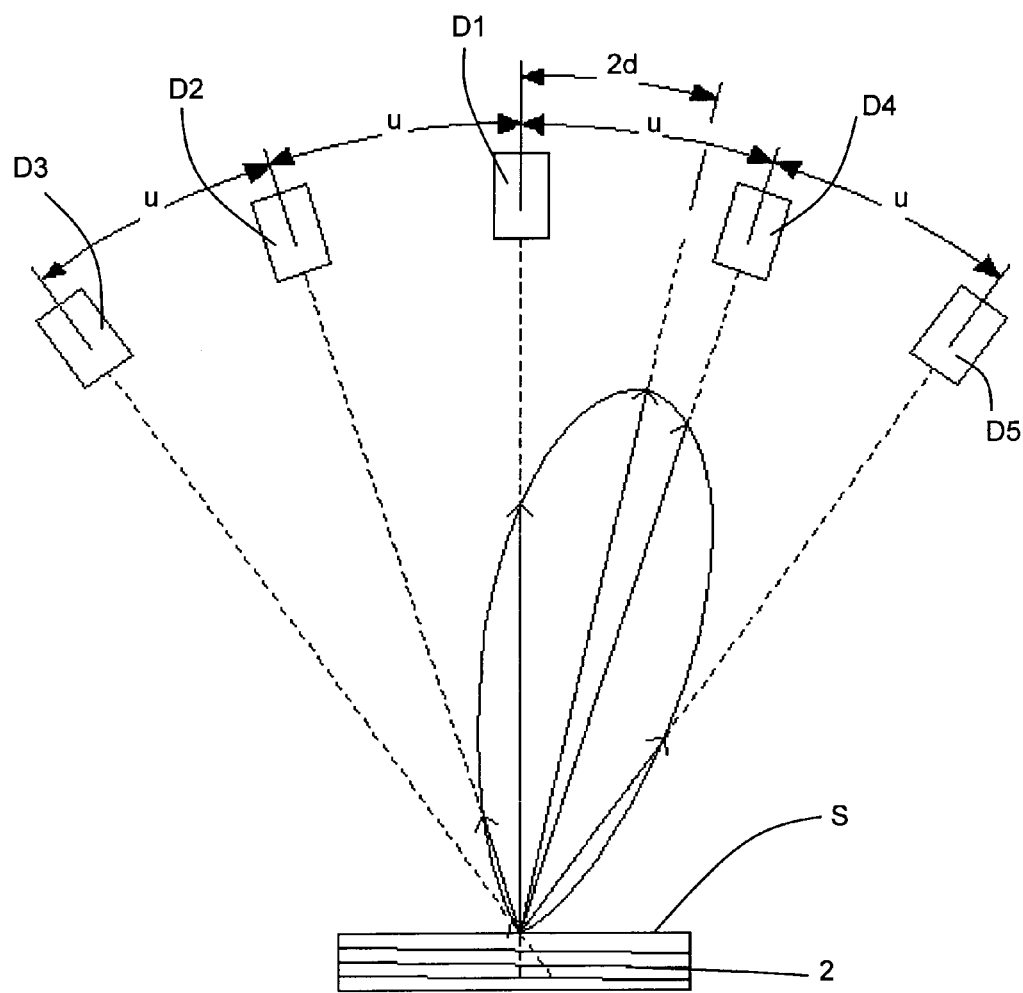

FIG. 19 shows an embodiment analogous to the one of FIG. 4;

FIG. 20 shows an amplitude profile of the reflected light in the plane of incidence;

FIG. 21 illustrates specular reflection with the light normally incident upon the wood surface;

FIG. 22 shows an orthogonal section thru the cone of specular reflection;

FIG. 23 graphically shows the polarisation properties of specularly reflected light;

FIGS. 24 and 25 illustrates the section of the reflected light cone for different fibre orientation;

FIG. 26 shows a multiple detector arrangement; and

Figure 27:
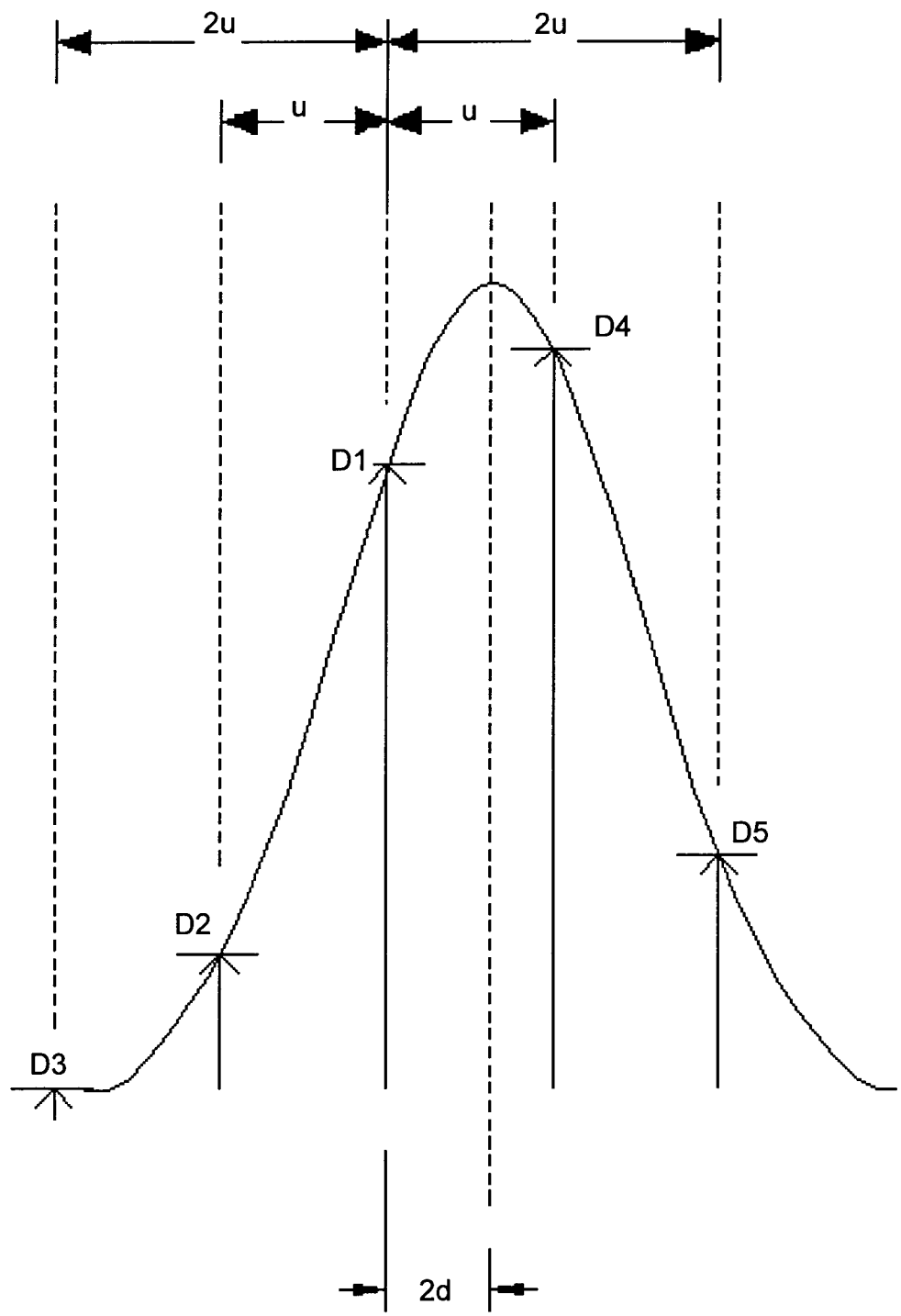

FIG. 27 shows the relative signal amplitudes across the detector of FIG. 26.

With reference to the accompanying drawings, the numeral 1 denotes as a whole an apparatus for identifying the orientation of wood fibres 2, made in accordance with the present invention.

However, before describing the apparatus 1 it is appropriate to examine the method which said apparatus 1 is designed to implement.

The method for identifying the orientation of wood fibres 2 according to the present invention is based on studies carried out which allowed a link to be revealed between the polarisation of a beam of light reflected by a fibre 2 and the spatial orientation of that fibre 2.

In particular, said method may be first better conceptualised with reference to a simplified model as regards the physical reflection of the light by the wood 3.

According to this model, the reflection of the light by a set of wood fibres 2 may be compared with the reflection of a partly diffusing specular cylinder. Moreover, according to this model, the reflected light comprises two main components, a diffuse component (omnidirectional) and a specular component (directional) corresponding to the reflection which can be obtained from a cylindrical reflector.

This simple geometric model for the reflection of light by the wood 3 was already previously proposed by this inventor in U.S. Pat. No. 4,606,645.

However, compared with what was previously proposed, according to the present invention the model has been extended so that it also takes into account the optical property of polarisation.

In the wood 3, the specular component of the reflection is caused by the anisotropic fibrils which form the cell walls of the wood 3, said fibrils mainly consisting of cellulose anisotropic molecule chains. It is well known that this cellulose structure has birefringent properties. As is well known to experts in the sector, the polarisation of light striking a birefringent material is modified by the specular reflection, so that the reflected light is repolarised.

In particular, the present invention is based on the idea that when linearly polarised light is reflected by a birefringent material, the polarisation of the reflected light is modified according to the angle existing in space between the incident light polarisation plane and the actual optical axis of the wood 3 cells.

According to this extended model of the reflection of linearly polarised light, the reflected light contains information about the angle existing between the axis (optical and longitudinal) of the wood 3 cells, and the incident light polarisation plane. Therefore, said angle indicates the orientation of the fibre 2 relative to the reference consisting of the incident light polarisation plane.

Thus, according to the present invention, the orientation of wood fibres 2 is identified by detecting and analysing the light reflected by the surface of the wood 3 after illumination with one or more beams of light polarised in a predetermined plane.

Before facing the method of the present invention is then useful a deep analyses of the extended model on which it is based, with the aid of enclosed FIGS. 20-27.

When a incident light hit a piece of wood, light reflected from wood is the sum of two major components: a diffuse reflected component and a specular (mirror like) reflected component. The maximum amplitude ratio of specular/diffuse reflection lies in the range 1/2.5 to 1/10 depending upon the species type and surface finish.

As regard diffuse reflection characteristics, it is to be noted that when a narrow beam of light is incident on the surface, light is omnidirectionally reflected from the point of incidence. FIG. 20 shows an amplitude profile of the diffused reflected light in the plane of incidence. As it can be seen in the figure, the primary component Dr (defined as the one with maximum amplitude) is perpendicular to the surface S independently of the angle of incidence of the incident light L and wood fibre orientation. Furthermore, the amplitude profile is symmetric with rotation around the primary component axis.

The amplitude of reflected light Drp in generic direction p is given by:

$$Drp \sim Dr \cos(p)$$

where Dr is the amplitude of the primary component.

Moreover, the circle in FIG. 20 represent the envelope of diffuse reflection.

Finally, significantly, plane polarised light incident on wood is de-polarised by diffuse reflection.

As regard specular reflection characteristics, it is to be noted that, to a first order, specular reflection of light from wood can be modeled by reflection from a cylindrical reflector whose axis is aligned with the wood fibre axis. The directionality of the reflected light is thus a direct function of the cylinder axis orientation with respect to incident illumination.

Furthermore, reflected light is composed by two groups of components too: primary components and secondary components.

The primary components of specular reflection (that is the ones with maximum amplitude) lie within the surface of a "cone of reflection", where the axis α of the cone is aligned with the cylinder axis; and the apex angle of the cone C, C' is given by:

$$\text{Apex angle} = (180° - 2d)$$

where d is the angle of incidence between the cylinder axis and the incident light, expressed in degrees.

FIG. 21 illustrates specular reflection with the light normally incident upon the surface. For analysis, the cylinder (fibre) axis orientation (vector V inclined of an angle v with respect to the nominal fibre orientation) can be represented by a surface vector S (inclined of a rotation angle s with respect to the nominal fibre orientation in a plane orthogonal to the incident beam) and an orthogonal vector D (inclined of a dive angle d with respect to the nominal fibre orientation in a plane thru the incident beam), where:

$$V = \sqrt{S^2 + D^2}$$

In FIG. 21 two different case are shown.

According to a first one, the two angles are: s=0, d=0

Here, the angle of incidence of the incident light L to the cell axis is 0°, and apex angle of the cone is 180°, so the surface of primary reflection lies in a plane C thru the incident beam axis.

Should the angles be: s≠0, d=0, the plane surface remains plane and rotates around the incident beam axis by angle s.

According to the second case of FIG. 21 (shown in the left part of the figure) the angles are: s=0, d≠0. Here, the angle of incidence is d and the apex angle of the cone is 180°−2d, so the surface of primary reflection lies in a cone C'.

Finally, should the angles be: s=0, d≠0, the cone axis rotates around the incident beam axis by angle s.

As far as secondary components of specular reflection are concerned, the detailed microstructure of wood cell outer (and inner) walls gives rise to a departure from the first order cylindrical reflector model above disclosed. In fact, specular components are symmetrically scattered around the primary specular surface (light cone) as illustrated by FIG. 22 which shows an orthogonal section thru the cone of specular reflection, illustrating the angular and amplitude distribution of secondary specular components around the primary one.

The secondary component amplitudes Ap are related to the primary component amplitude A by:

$$Ap = A \cos^n(p)$$

where p is the angle of deviation from the primary and the numerical value of n is species and wavelength dependent, typically lying between 10 and 20.

In FIG. 22 the curved closed line represents the envelope of specular reflection.

Given that, polarisation of specularly reflected light from wood can be analysed according to the extended model of light reflection.

When plane-polarised (or linearly polarised) light L is incident upon wood the specularly reflected light RL comprises two plane polarised components; one, PX2, polarised in a plane pX2 parallel to the wood cell axis, the other, PX3, polarised in a plane pX3 perpendicular to the wood cell axis (see FIG. 23).

The orientation of PX2 is rotated by angle s relative to the orientation of the incident light polarisation pS, while the orientation of PX3 is thus rotated by s+90°.

The amplitudes of these components are related to the incident amplitude I by:

$$PX1 \sim I \cos^2(s)$$

$$PX2 \sim I \sin^2(s).$$

These reflection features relate to both primary and secondary components.

FIGS. 24 and 25 illustrates the sections of the light cone respectively for d=0 and d≠0 with respect to a detector D assembly.

It must be noted that the amplitude received by the detector reduces with increasing d; this reduces the signal/noise ratio of the signals.

As better disclosed in the following, the multiple detector arrangement (D1-D5) shown in FIG. 26 can be used to alleviate this reduction in signal/noise when d≠0.

In the example shown detector D4 yields the largest signal, so the signals from detector D4 should be used to derive the value of s.

Note that this arrangement can also be used to derive the value of d.

FIG. 27 shows the relative signal amplitudes across the detectors. The value of 2d can be derived in terms of the detector distribution angle u by simple interpolation.

The arrangement yields the values for s and d, allowing computation of the vector angle v. But that will be better disclosed in the following.

Coming now to the method of the present invention, it involves first the operating steps of generating at least one beam of light 4, and projecting the beam of light 4 onto a surface of a piece of wood 3 to illuminate a zone where the orientation of the wood fibres 2 will be identified. In particular, the beam of light 4 is generated polarised in a first predetermined polarisation plane pS.

In the context of the present invention, the term beam of light 4 refers to a light beam (preferably laser light) having a predetermined cross-section and intended to detect the orientation of the fibres 2 at a specific limited zone of the surface of the wood 3 (a zone which may also comprise a plurality of cells, which, however, being adjacent, on average have the same orientation).

Projection of the beam of light 4 onto the surface of the wood 3 generates, from the illuminated zone, diffusely reflected light which is non-polarised and specularly reflected light which is polarised. According to the optical model which is the basis of the present invention, the latter reflected light comprises two components of plane polarised light. In particular, it comprises a primary component which is polarised in a second polarisation plane pX2 parallel to the optical axis of the fibre(s), and a secondary component which is polarised in a third polarisation plane pX3 perpendicular to the optical axis of the fibres. Amplitudes of these polarisation components depend upon the angle s between the wood cell optic axis (which is indicated by vector V) and the polarisation plane pS of the incident illumination; in particular amplitude of the component polarised in the second plane pX2 is proportional to $\cos^2 s$ and the amplitude of the component polarised in the third plane pX3 is proportional to $\sin^2 s$.

The method involves then the operating step of detecting the linearly polarised reflected light 5 using suitable detection devices 6 equipped with suitable polarised filters (described in more detail below) to establish the orientation of the second polarisation plane pX2, and to identify the orientation of the fibres 2 in the illuminated zone, at least indirectly, based on the orientation in space of the second polarisation plane pX2 of the reflected light 5 detected It should be noticed that the statement that identification may be indirect means that identification of the orientation of the fibre 2 may be performed either by actually identifying the second polarisation-plane pX2 to which the fibres 2 are parallel, or by using the readings taken (which depend on said plane) to directly calculate the orientation of the fibre 2.

Since the situation changes if d=0 or d≠0, the first case will be explained first being the simpler one.

In light of the above, generally speaking the step of identifying the orientation of the fibres 2 at the illuminated zone involves identification of the orientation of the fibres 2 as the orientation in space of a straight line parallel to the polarisation plane of the primary component of the reflected light 5 detected (that is to say, to the second polarisation plane pX2).

According to the preferred embodiment of the present invention, the step of detecting the polarised reflected light 5 involves on one hand detecting the intensity of components of the reflected light 5 according to a plurality of separate reference polarisation planes P1, P2, P3, (P4), and, on the other hand, identifying the orientation of the second polarisation plane pX2 of the reflected light 5 as a combination of the intensities of said components detected.

In particular, the step of detecting the intensity of the components of the reflected light 5 involves observation of the illuminated zone according to at least one predetermined direction of observation 7 (described in more detail below) and the detection of first components of the reflected light 5 according to a plurality of separate reference polarisation planes P1, P2, P3, (P4).

It should be noticed how in the present invention the term polarisation plane always refers to the entire family of parallel planes. What matters is not the absolute position in space, but the orientation of the plane in space.

Consequently, advantageously, the reference polarisation planes P1, P2, P3, (P4) are selected belonging to a bundle and identifying a shared intersecting straight line 8 having a predetermined direction of extension (again, what matters is the direction of the straight line to infinity). In particular, the predetermined direction of extension of the shared straight line 8 of the bundle of reference polarisation planes P1, P2, P3, (P4) is advantageously selected perpendicular to the observed zone of the surface of the piece of wood 3.

Figure 2:
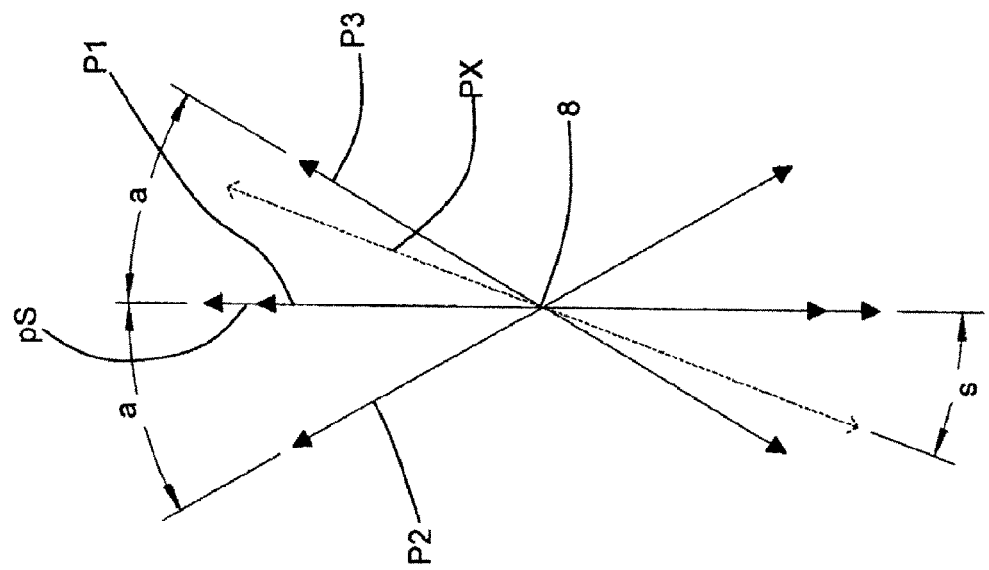
FIG. 2 shows the arrangement of a plurality of planes which are significant for application of the method according to the present invention.
Figure 14:
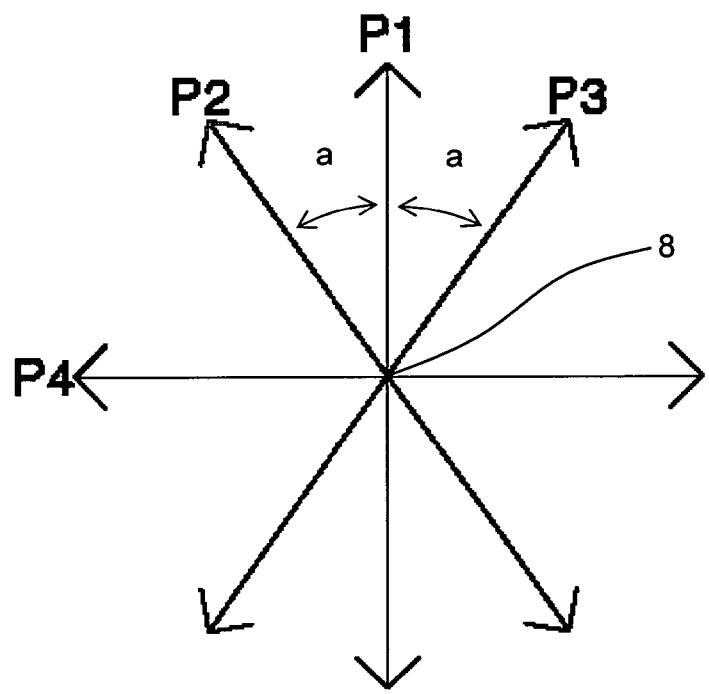
FIG. 14 shows an alternative arrangement of a plurality of planes which are significant for application of the method according to the present invention.
Figure 15:
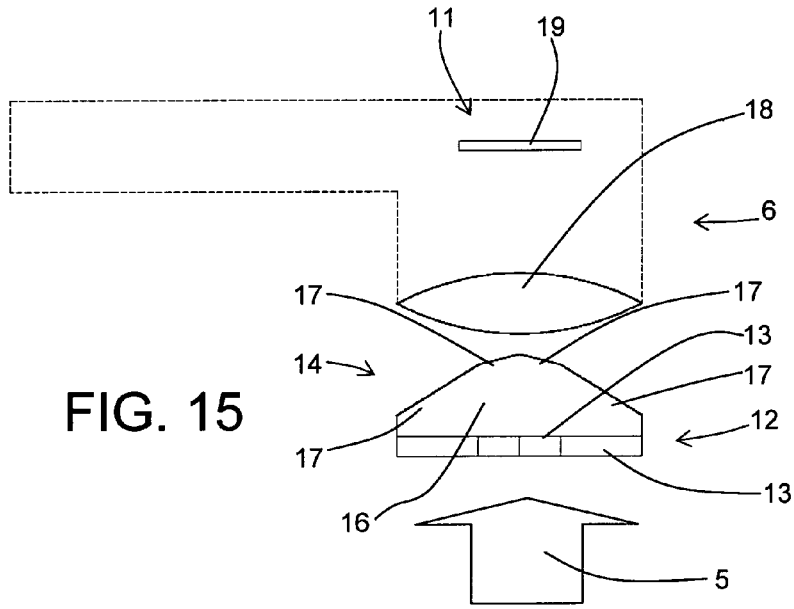
FIG. 15 is a schematic view of a detail of a fourth apparatus made according to the present invention.

Said situation is schematically illustrated in FIGS. 2 and 14 which represent, respectively, a reference system with three reference polarisation planes P1, P2, P3, and a reference system with four planes P1, P2, P3, P4. In both of the cases illustrated, each double-headed arrow with a continuous line represents one of the reference planes, according to an axis of observation entering the drawing and perpendicular to the surface of the piece of wood. In particular, in the case in FIG. 2 there is a first, central reference plane P1 and two lateral reference planes P2, P3 respectively set relative to the plane P1 at an angle a in the anti-clockwise direction and an angle a in the clockwise direction. In other words, the two lateral planes are rotated relative to the central plane through an angle of rotation which is identical in opposite directions. Preferably, the absolute value of the angle between the central plane and the lateral planes is between 10° and 45°. Finally, in the case in FIG. 14 there is an additional reference plane P4, perpendicular to the plane P1.

This last reference plane P4 is not essential to essence of the present invention, but in combination with P1 is useful for detecting extreme grain distortion and localised defects. In fact, the difference between the P1 signal and P4 signal is at a maximum when s=0°, falls to a minimum when s=45° and again rises to maximum when s=90°. It also falls to a minimum when the incident light 4 falls on a diffuse surface (e.g. the face of a knot). This provides a useful gating signal for declaring a point under inspection "defect", or "invalid for grain angle measurement".

Again according to the preferred embodiment of the present invention, the central reference plane P1 is selected such that it coincides with the incident light first polarisation plane pS.

In this way, if the incident light first polarisation plane pS is selected parallel to the nominal direction of extension of the wood fibres 2 (that is to say, the longitudinal direction of the piece of wood 3), if the actual orientation of the fibres 2 is the nominal one, the second polarisation plane pX2 of the reflected light 5 will coincide with the first reference plane P1, generally making detection simpler even in the case of limited deviations relative to the nominal condition.

FIG. 2 also shows with a dashed line a possible orientation of the wood fibres 2 at the illuminated zone relative to the polarisation reference system. Said fibres 2 are set at an angle s, to be identified, to the first polarisation plane pS (which coincides with the central reference plane P1) and, consequently, with the nominal fibres orientation.

As already indicated, the orientation of the fibres 2 is the unknown factor which the present invention aims to identify by means of mathematical processing of the intensity of the light which can be detected, along a predetermined direction of observation 7, in each reference polarisation plane.

Mathematical analysis of the physical situation illustrated in FIG. 2 indicates that the value of the intensity of the light polarised in each of the four reference planes is proportional to the overall intensity of the signal based on the following expressions: (please check the right equation as regard the exponents)

$$i1 \infty \cos^4(s) + \sin^4(s) + Dr$$

$$i2 \infty \cos^2(s) \cdot \cos^2(s+a) + \sin^2(s) \cdot \sin^2(s+a) + \frac{\cos^2(a)}{\pi} + Dr$$

$$i3 \infty \cos^2(s) \cdot \cos^2(s-a) + \sin^2(s) \cdot \sin^2(s-a) + \frac{\cos^2(a)}{\pi} + Dr$$

$$i4 \infty 2\cos^2(s)\sin^2(s) + Dr$$

where i1 is the intensity of the light detected according to the central reference plane P1, i2 is the intensity of the light detected according to the lateral reference plane P2, i3 is the intensity of the light detected according to the other lateral reference plane P3, and Dr, as said, is the component of the signal due to the non-polarised diffuse light, common to all of the detectors.

Moreover, from the above equations it is possible to mathematically establish that the function:

$$f(i1, i2, i3) = \frac{(i1-i2) - (i1-i3)}{(i1-i2) + (i1-i3)}$$

provides a linear measurement of the angle s formed by the wood fibres 2, relative to a range of predetermined values of the angle a.

More specifically, if k is an arithmetic constant, the angle s may be calculated with the formula:

$$s = k * a * \frac{(i1-i2) - (i1-i3)}{(i1-i2) + (i1-i3)}.$$

Consequently, based on the measurement of the intensity of the light detected in each reference polarisation plane, it is possible to calculate the angle between the fibres 2 (or the second polarisation plane pX2 parallel to them) and the reference plane P1.

The intensity detected in each reference polarisation plane will be greater the smaller the angle is between the reference plane and the second polarisation plane pX2. Therefore, in the situation illustrated in FIG. 2, it will be i3>i1>i2.

Up to this point reference was made to a method involving observation of the illuminated zone along a single specific direction of observation 7. Consequently, the information which the method described so far allows to be obtained is the orientation of the fibres 2 which can be seen along said direction of observation 7. That is to say, the orientation of the projection of the fibres 2 in a plane perpendicular to the direction of observation 7. Therefore, when the direction of observation 7 is perpendicular to the surface of the piece of wood 3, the angle s is the angle which the wood fibres 2 form relative to the surface of the plank. Therefore, as explained at the beginning, the method described up to now allows complete identification of the orientation of the fibres 2 only if they lie in a plane perpendicular to the direction of observation 7.

Figure 5:
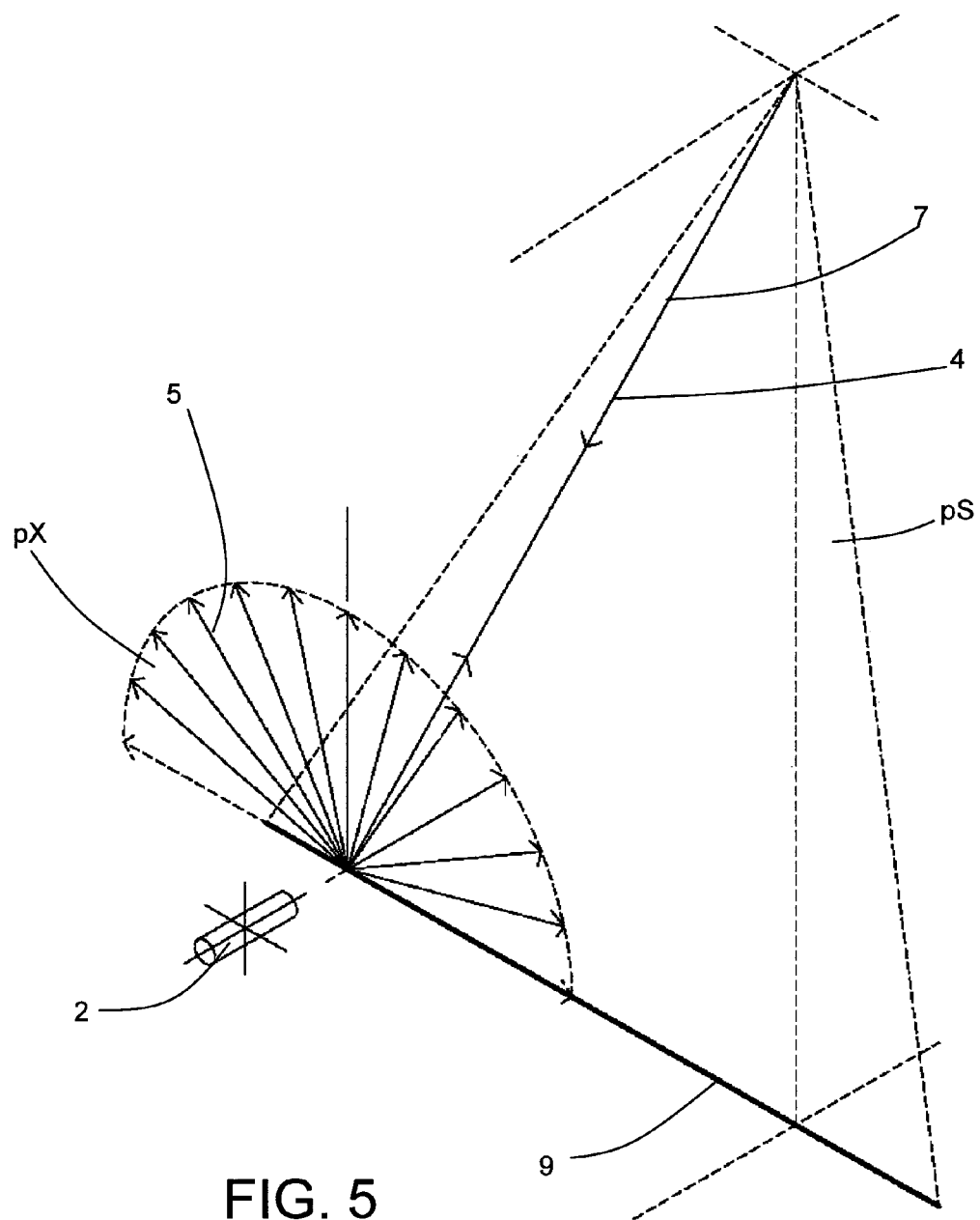
FIG. 5 illustrates the method according to the present invention with reference to a first spatial orientation of the fibre 2.
Figure 7:
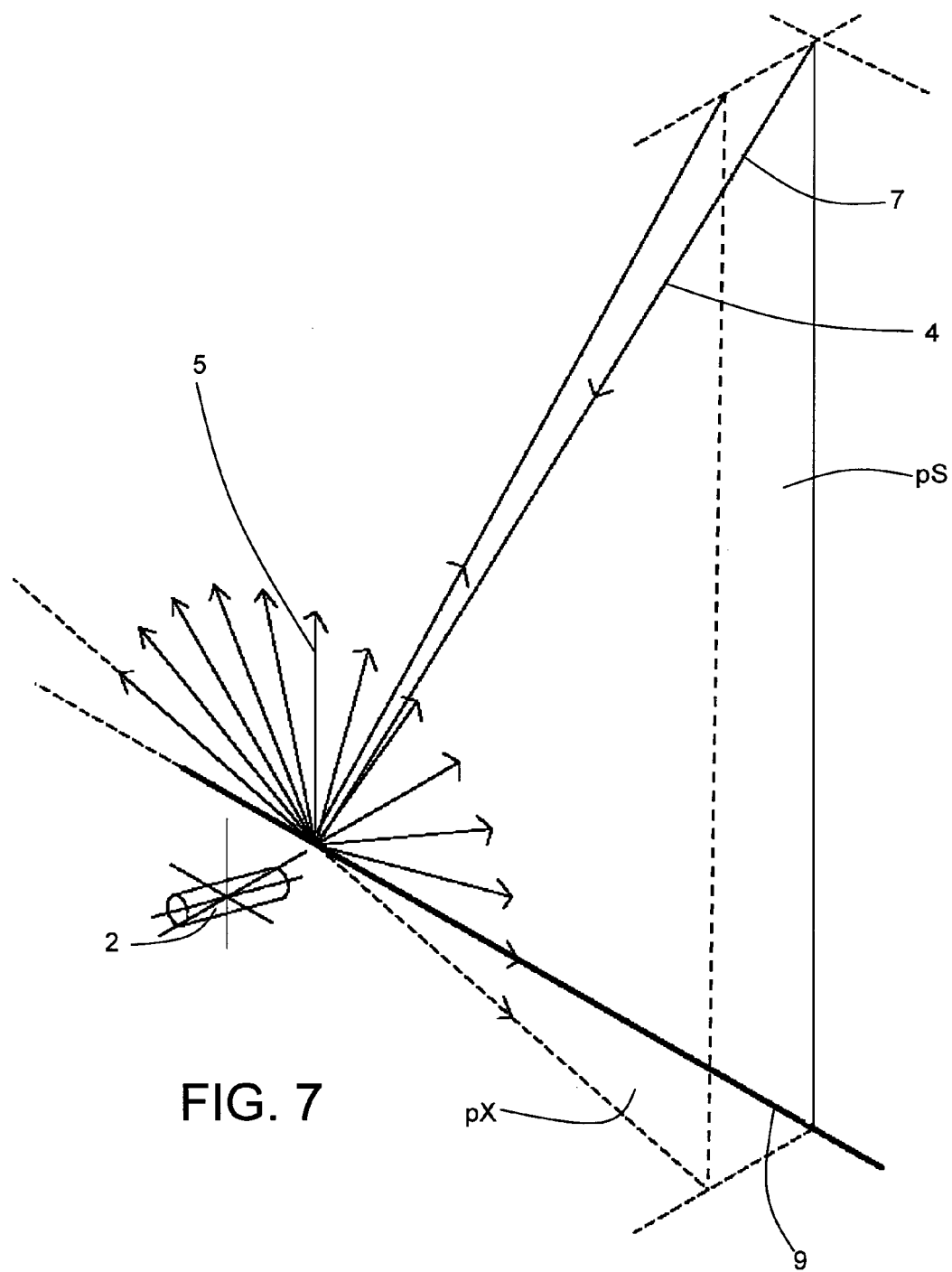
FIG. 7 illustrates the method according to the present invention with reference to a third spatial orientation of the fibre 2.
Figure 11:
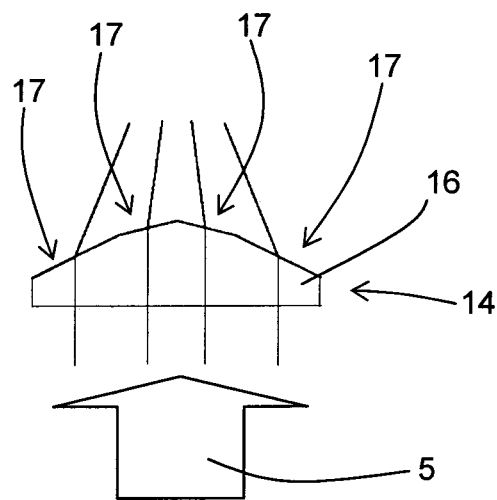
FIG. 11 shows a third example of a splitter for a beam of light used in the present invention.
Figure 12:
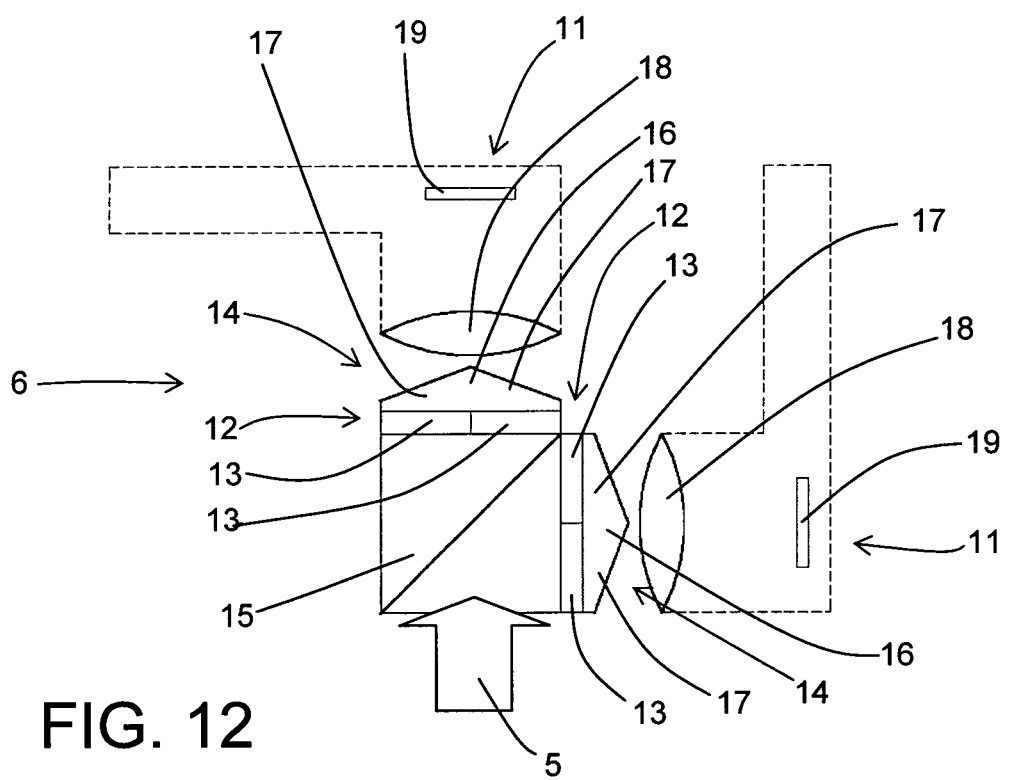
FIG. 12 is a schematic view of a detail of a second apparatus made is according to the present invention.
Figure 13:
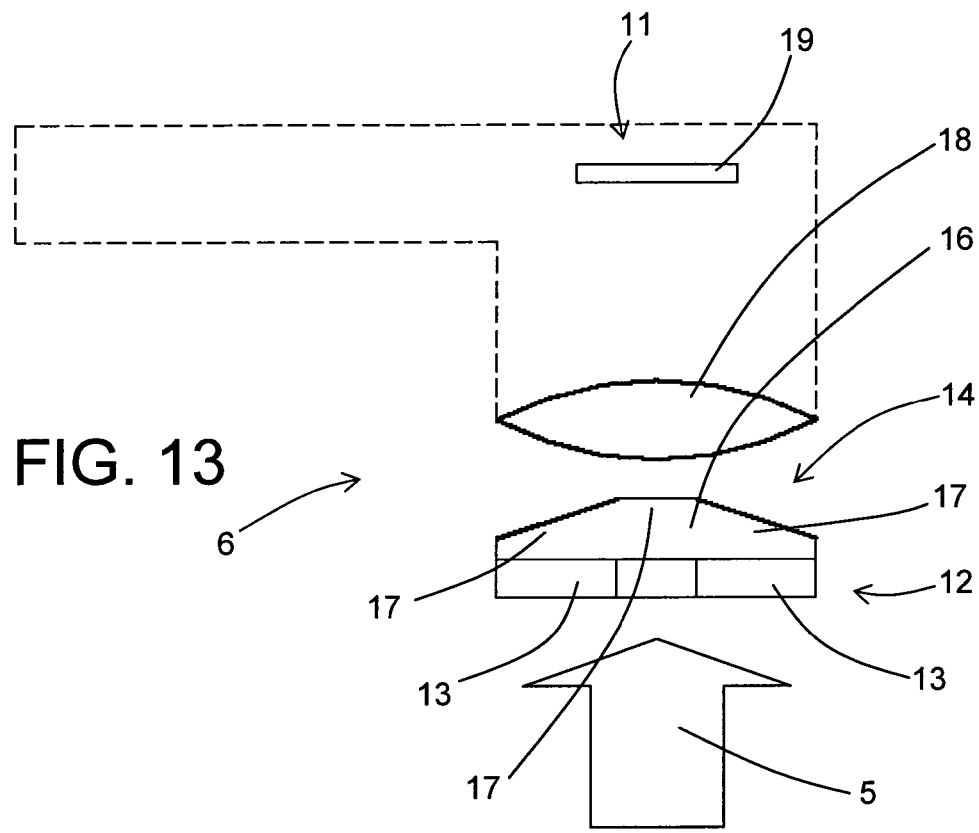
FIG. 13 is a schematic view of a detail of a third apparatus made according to the present invention.

Two examples of this situation are represented in FIGS. 5 and 7, where the fibres 2 extend in the surface plane of the piece of wood 3 and where the direction of observation 7, like the incident beam of light 4, lies in a plane perpendicular to the surface of the piece of wood 3. In both cases the first polarisation plane pS is also perpendicular to the surface of the wood 3, as well as parallel to the nominal direction of the fibres 2 (which is usually assumed parallel to the wood surface).

In particular, FIG. 5 shows the case of a fibre 2 whose orientation coincides with the nominal direction. In this case the second polarisation plane pX2 coincides with the first polarisation plane pS. Consequently, the readings of the various intensities will give i1>i2=i3.

In contrast, FIG. 7 shows the case of a fibre 2 which forms an angle s relative to the nominal direction. In this case the second polarisation plane pX2 also forms an angle s relative to the first polarisation plane pS.

Figure 6:
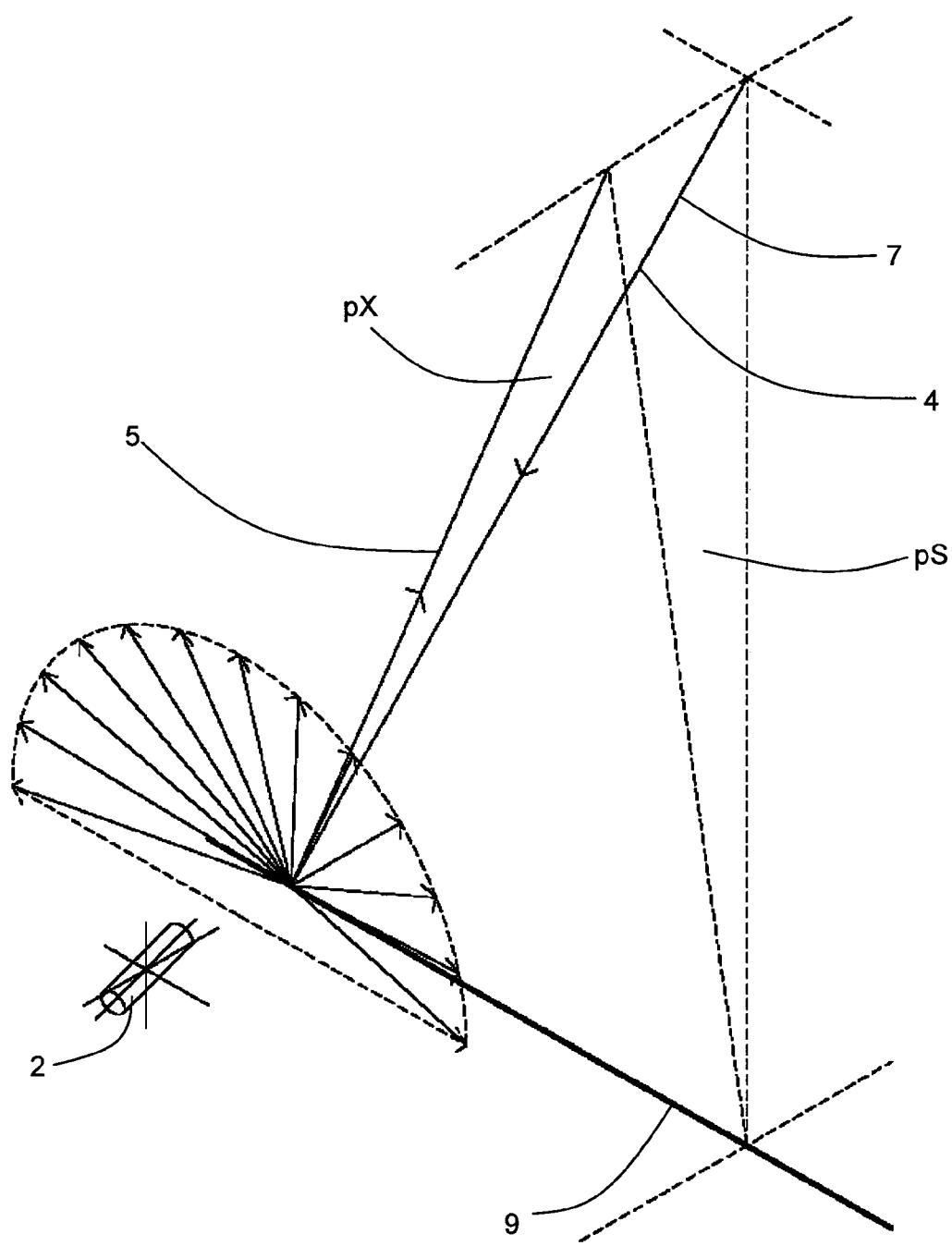
FIG. 6 illustrates the method according to the present invention with reference to a second spatial orientation of the fibre 2.

The situation changes when the fibre 2 does not lie in the plane perpendicular to the direction of observation 7, as in the case illustrated in FIG. 6 (and in FIGS. 21, 23, 26, 27 above described), where the examination conditions are the same as in FIGS. 5 and 7, but instead it is angled upwards relative to the surface of the piece of wood 3. In this case, observation according to a direction perpendicular to the surface does not allow identification of the angle of the fibre 2 relative to the surface, but only provides an indication that the fibre 2 seems to be aligned with the nominal direction. Indeed, any line developing in a plane satisfy the condition of being parallel to it.

To overcome said disadvantage, and identify the overall orientation in space, the present invention involves additional steps.

As said above, in fact, when d≠0, the primary component of the specular reflection will be deflected away from the direction of observation by an angle of 2d. This results in a reduction in contrast between the detected specular and diffuse reflection components with a consequent reduction in signal/noise ratio.

In order to alleviate this reduction in signal/noise, according to the method the step of detecting the reflected light 5 is repeated, observing the illuminated zone according to a plurality of predetermined directions of observation 7 set at an angle to each other to identify a plurality of additional spatial components of the orientation of the fibres 2 (which are no more than the projection of the orientation in planes perpendicular to the direction of observation 7), as well as the spatial orientation of the fibres 2 being identified as a combination of said plurality of components.

Said situation is schematically illustrated in FIG. 4 which shows three main detection devices 6 and two auxiliary devices 6a, which observe the same portion of the surface of the piece of wood 3 (the illuminated portion) according to five different directions of observation 7.

In particular, said directions of observation 7 are advantageously selected so that they are coplanar and lie in a plane perpendicular to the surface of the piece of wood 3 and comprising the nominal direction of extension of the fibres 2. Moreover, as already indicated, at least one of the directions of observation 7 is selected so that it is perpendicular to the surface of the piece of wood 3. Moreover, advantageously, the directions of observation 7 form a plane parallel to the first polarisation plane pS of the beam of incident light 4.

It should also be noticed that whilst a reading may also generally be obtained only with the three main devices 6, the two auxiliary devices 6a may allow an improved reading in the case of fibres 2 which are at a particularly significant angle (that is to say such that the second polarisation plane pX2 falls outside the space delimited by the three central devices).

Moreover, in accordance with the present invention, the reference planes P1, P2, P3 (and P4 if present) of each device may either all have the same absolute orientation in space, or all have the same orientation relative to the direction of observation 7 (which, in this case, advantageously will coincide with the shared straight line 8 of the bundle formed by them).

However, in both cases, the result achieved is similar. Each device supplies an indication regarding the projection of the direction of extension of the fibre 2 in a plane perpendicular to the direction of observation 7. As a result, the three-dimensional orientation of the fibre 2 may be obtained with a combination of the components identified in this way (see also FIGS. 26-27 above).

A more detailed explanation of that is furnished with reference to FIG. 19 which substantially reproduce the situation of FIG. 4.

In this arrangement, a number of detector devices (6A, 6B, 6C, 6D and 6E) are disposed to view the incidence of the light from the plane polarised source 10 with the wood surface, in a plane parallel to the nominal grain direction of the piece. The detector devices are placed equidistant from the incidence and disposed symmetrically around the central detector device (6A) with uniform angular separation u.

In cases where d≠0 the primary specular reflection component Dr is deflected by angle 2d from the surface normal. The scattered specular components will be distributed around this angle with amplitudes in accordance with the above indicated equation.

With this arrangement the values of specular reflection components received by the various detector devices (6A, 6B, 6C, 6D and 6E) will vary in accordance with the deflection angle 2d, whereas the component of diffuse reflection will be independent of angle 2d.

Consequently, for any detector the signal function I:

$$I=(i1+i2+i3) \text{ (or } I=(i1+i2+i3+i4) \text{ if applicable)}$$

is a measure of the total (specular+diffuse) light received by that detector. The detector yielding the maximum value for 1 will be the one nearest to the deflection angle 2d (detector device 6D in the FIG. 19) and will offer the best signal/noise ratio. The signals derived by that detector should be applied to equation $$s = k*a* \frac{(i1-i2)-(i1-i3)}{(i1-i2)+(i1-i3)}$$

to yield the best value for s.

But, as said, a further feature of this arrangement is that it allows measurement of d, the diving component of the grain angle vector.

The angular location of the reflective peak (angle 2d) in the detection plane can be derived by simple mathematical interpolation from the values for signal I received by each of the various detectors (see above).

The form of the specularly reflected light allows a simple linear interpolation between each of the various detector signals according to formula $$Drp \sim Dr \cos^n(p)$$

to derive the intersection angle 2d; which in turn yields the diving grain angle d.

The arrangement of FIG. 19, with simplistic signal processing thus yields measures of each component of the grain vector, s, and d, allowing calculation of the grain vector angle v.

Advantageously, the method disclosed may be implemented by carrying out the operating steps described up to now for a plurality of separate beams of light which illuminate different zones of the surface of the wood 3, and in particular for a plurality of coplanar beams of light which together form on the surface of the piece of wood 3 an overall illuminated zone with linear extension 9.

Moreover, even more advantageously, the method may involve the operating step of feeding the piece of wood 3 along a feed trajectory T and repeating all of the other steps described up to now for a plurality of illuminated zones located one after another along the piece of wood 3 (spaced out according to a predetermined step). In this case, the overall illuminated zone is preferably generated across the feed trajectory T so that it covers the entire width of the piece of wood 3 transversally to the feed trajectory T.

Figure 3:
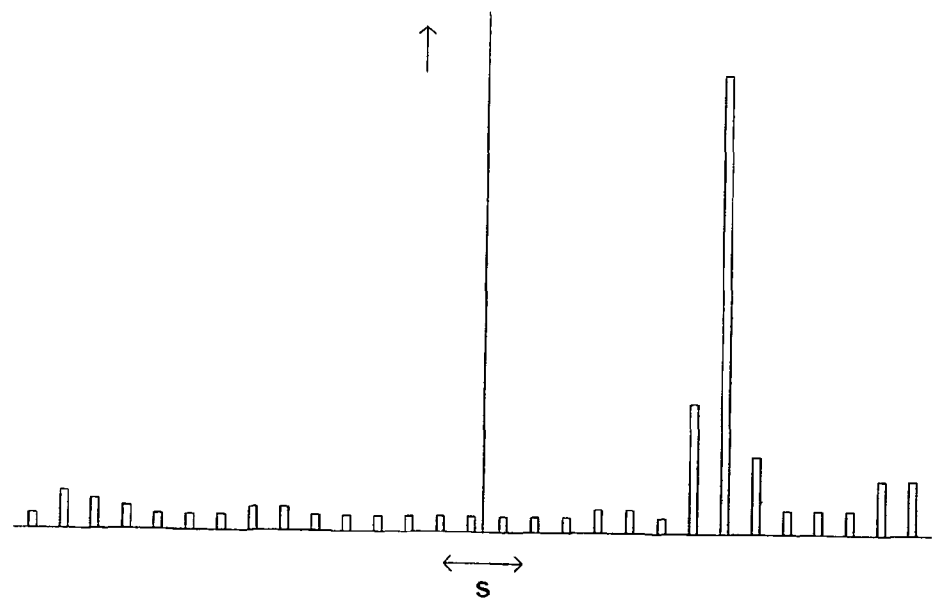
FIG. 3 is a graph of an example of the distribution of the orientation of the fibre 2 inside a piece of wood examined according to the present invention.

By acting in this way it is possible to map the orientation of the fibres 2 on the entire surface of a piece of wood 3. Said mapping can then be used to identify the overall quality of the piece of wood 3. FIG. 3 shows an example of distribution of the orientation of fibres 2 according to the angle s formed relative to the nominal direction, in the case of a piece of wood 3 in which the fibres 2 lie in the surface plane. The x-axis indicates the angle s of deviation from the nominal direction, whilst the y-axis shows the number of points of the surface examined in which the fibres 2 form said angle s relative to the nominal direction. The highest peaks represent the main orientation of the fibres 2, whilst the lowest ones represent the presence of localised defects.

The method described up to now may be implemented with any apparatus 1 suitable for the purpose. However, hereinafter several preferred embodiments invented by this inventor are described. Each of the following apparatus is advantageously programmed in order to execute the method of the present invention.

An apparatus 1 for identifying the orientation of the fibres 2 in a piece of wood 3 using the method described above usually comprises means (not illustrated) for supporting a piece of wood 3 to be examined, a light source 10, a detection device 6 and a processing device (not illustrated) which is operatively connected at least to the detection device 6 for processing what is detected and identifying the orientation of the wood fibres 2 at the illuminated zone.

The light source 10 is usually a laser source and is able to generate at least one beam of light 4 polarised in a first polarisation plane pS and, in practice, can project said beam 4 towards the piece of wood 3 supported by the supporting means.

The detection device 6 in turn comprises at least a first detector 11 facing towards the supporting means so that, after reflection of the beam of light 4 on the piece of wood 3, in practice, according to its own direction of observation 7, it detects the light coming from the zone of the piece of wood 3 illuminated by the beam of light 4. The detection device 6 also comprises means 12 for filtering, according to its polarisation, the light detected by the first detector 11.

According to the present invention, the filtering means 12 comprise a plurality of polarised filters 13 designed to filter the light coming from the illuminated zone of the piece of wood 3, according to a plurality of respective separate reference polarisation planes P1, P2, P3 and P4. In turn, the first detector 11 comprises means for detecting the intensity of the light detected in each of the reference polarisation planes P1, P2, P3, (P4).

Moreover, advantageously, the detection device 6 comprises splitter means 14 (e.g.: a beam splitter) for evenly splitting the light detected on the detection means.

In a first embodiment illustrated in FIGS. 8, 9, 10 and 12, the splitter means 14 comprise one or more reflective/refractive elements 15 such that they substantially refract one half of the intensity of a beam of light striking them (substantially making it continue beyond, parallel with itself) and substantially reflect the other half of the intensity of the beam. In the accompanying drawings the reflected part of the beam continues on its path along a direction perpendicular to the incident direction (the reflective/refractive element 15 is set at 45° angle to the entering beam).

FIG. 10, which shows the internal structure of a detection device 6, illustrates the combined use of three elements 15 of this type to split a beam detected into four substantially identical beams each with an intensity equal to one quarter of the intensity of the beam detected. Each of the four beams obtained in this way is then filtered by a specific polarised filter 13 and focused on a respective detector by means of a suitable lens.

In alternative embodiments, illustrated in FIGS. 11, 12, 13 and 15, the splitter means 14 instead comprise a prismatic refractor 16 for the beam of light, having a plurality of operating portions 17 positioned side by side, their number being equal to the number of reference polarisation planes P1, P2, P3, (P4) (and the separate beams to be obtained as output). Each operating portion 17 causes a different deflection of a beam of light passing through it. In the embodiments illustrated in FIGS. 11, 12, 13 and 15, each prismatic refractor 16 has a face, facing towards the entering beam, which is flat and shared by all of the operating portions 17, whilst on the opposite side it has as many faces as there are output operating portions 17. The fact that each of said output faces is at a different angle relative to the input face means that out of each operating portion there comes a beam of light which has a different orientation and is therefore separate from the beams of the other operating portions 17. Each beam at output may then be focused, using one or more lenses 18, either on a different sensor or on different zones of the same sensor (described in more detail below).

However, the use of prismatic refractors requires precise apparatus 1 set up, which is not always easy to achieve, since one must be certain that the share of the beam which strikes each operating portion is substantially identical, so that the same energy arrives on each polarised filter 13.

FIG. 16 shows another problem, called "speckle", which arises when laser beams are used as incident beams. A laser beam consists of a plurality of separate beams of light positioned side by side and distributed unevenly in the laser beam section. Said situation is highlighted in FIGS. 16a and 16b which show the distribution of the individual beams of light within the laser beam. As can be seen; the more the laser beam is "widened", the more obvious its unevenness becomes.

This phenomenon too may be a significant problem during splitting of the beam of light detected in the various polarisation planes using a prismatic refractor 16 since, at the refractor 16 beam widening is advantageous but, given the unevenness of the laser beam, the part of the beam covering one operating portion may have an energy density that is much greater than that of the part of the beam covering a different operating portion. If this happens, a false reading is obtained relative to the orientation of the fibres 2 (which, as already indicated, is identified based on the intensity of the light detected in each reference polarisation plane P1, P2, P3, P4).

To overcome said possible disadvantages, in accordance with the present invention a special light beam prismatic refractor 16 was provided, which also has a plurality of operating portions 17 but in a number much greater than the splits to be obtained (FIGS. 17 and 18). In particular, the number of operating portions 17 is a whole multiple: of the number of reference polarisation planes P1, P2, P3, (P4), and the operating portions 17 are made so that identical portions are grouped together (in FIGS. 17 and 18 the numeral 17 used to label the operating portions is followed by a letter a, b, c or d to indicate that they belong to four different groups), in such a way that the number of groups of operating portions 17 is equal to the number of reference polarisation planes P1, P2, P3, (P4).

Each operating portion of a group therefore causes a deflection of a beam of light passing through it which is equal to those of the other portions of the same group and different to that of the operating portions 17 of the other groups.

Moreover, advantageously, the operating portions 17 are evenly distributed in the prismatic refractor 16 so that inserted between two successive operating portions 17 of the same group there is only one operating portion of each of the other groups. For example, FIG. 17 shows the case of a prismatic refractor 16 with sixteen operating portions 17 made with four different shapes. For each shape (group) there are four operating portions 17 evenly distributed across the width of the refractor 16

Figure 1:
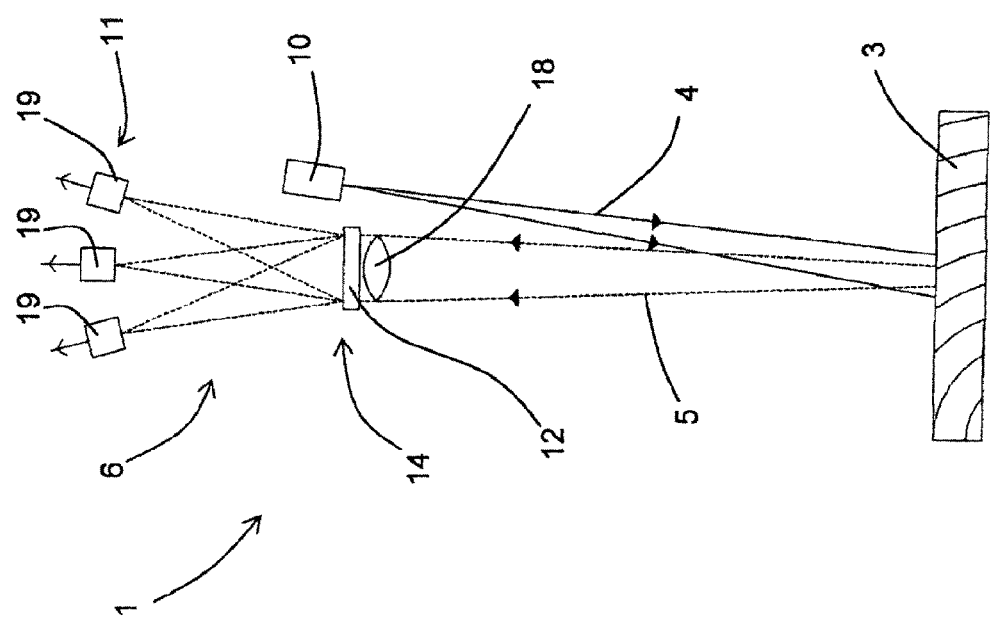
FIG. 1 is a longitudinal schematic view of the method and the apparatus according to the present invention.

As regards the polarised filters 13, depending on requirements they may be positioned either upstream (FIG. 18) or downstream (FIG. 10) of the splitter means 14 with reference to the direction of light propagation towards the first detector 11. In particular, as illustrated in FIG. 18, if prismatic refractors are used, the polarised filters 13 must be associated with each operating portion (with identical filters 13 for identical operating portions 17). As regards the sensors, the first detector 11 may comprise either a single sensor 19 with a plurality of operating zones 20 each intended to detect the intensity of the component of the light detected, polarised according to one of the polarisation planes (embodiment in FIGS. 13 and 15), or a plurality of sensors 19 each having one (FIGS. 1 and 10) or more operating zones 20 (FIG. 12), each operating zone 20 being designed to detect the intensity of the component of the light detected, polarised according to one of the polarisation planes.

Moreover, as illustrated in FIG. 4, in order to be able to evaluate the angle of the fibres 2 not just in one plane, but in three-dimensional space, the apparatus 1 may comprise a plurality of detection devices 6 each acting along its own direction of observation 7 (according to the methods indicated above).

Advantageously, the supporting means form a main plane in which the piece of wood 3 lies and the directions of observation 7 are selected so that they are coplanar in a plane perpendicular to the main plane in which the wood lies and they extend symmetrically relative to a direction coplanar with them, perpendicular to the main plane in which the wood lies and coplanar with the beam of light 4 (FIG. 4).

According to what was described relative to the method, the light source 10 may generate a plurality of beams of light, preferably aligned, the supporting means may also constitute means for moving the piece of wood 3 in the main plane in which it lies, and the processing device may be programmed to process what is detected and to identify the orientation of the wood fibres 2 at the illuminated zone each time the movement means have moved the piece of wood 3 forward by a predetermined step.

The present invention brings important advantages.

In its simplest embodiment it allows identification of the orientation of the wood fibres in the plane perpendicular to the observation plane.

In the more complex embodiments it allows identification of the orientation of the wood fibres at a three-dimensional level.

It should also be noticed that the present invention is relatively easy to produce and that even the cost linked to implementing the invention is not very high.

The invention described may be modified and adapted in several ways without thereby departing from the scope of the inventive concept.

Moreover, all details of the invention may be substituted with other technically equivalent elements and in practice all of the materials used, as well as the shapes and dimensions of the various components, may be any according to requirements.

The invention claimed is:

1. A method for identifying the orientation of wood fibres in a piece of wood, characterised in that it comprises the operating steps of:
   generating at least one beam of light (4), said light being polarised in a predetermined first polarisation plane (pS);
   projecting the beam of light (4) onto a surface of the piece of wood (3) to illuminate a zone of the surface and generate, from said zone, diffuse light without polarisation and reflected light (5) linearly polarised at least in a second polarisation plane (pX2);
   detecting said reflected light (5), said detecting step including detecting the intensity of components of the reflected light (5) with respect to at least three separate reference polarisation planes (P1), (P2), (P3); and
   identifying the orientation of the wood fibres (2) in said zone at least indirectly based on the orientation in space of the second polarisation plane (pX2) of the reflected light (5).

2. The method according to claim 1, characterised in that the step of identifying the orientation of the fibres (2) of the illuminated zone involves identification of the orientation of the fibres (2) as the orientation of a straight line parallel to the second polarisation plane of the reflected light (5) detected.

3. The method according to claim 2, characterised in that the second polarisation plane (pX2) of the reflected light (5) is identified as a combination of the intensities of said components.

4. The method according to claim 3, characterised in that the step of detecting the intensity of the components of the reflected light (5) involves observation of the illuminated zone according to a predetermined direction of observation (7) and detection of first components of the reflected light (5) according to a plurality of separate reference polarisation planes (P1), (P2), (P3), (P4) belonging to a bundle and identifying a shared straight line (8) which has its own predetermined direction of extension.

5. The method according to claim 4, characterised in that the first components are detected according to the three reference polarisation planes (P1), (P2), (P3), said three planes being one central plane and two lateral planes rotated relative to the central plane through an angle of rotation which is identical in opposite directions, the absolute value of the angle between the central plane and the lateral planes being selected between 10° and 45° and in that the central reference plane is selected so that it coincides with the first polarisation plane (pS).

6. The method according to claim 5, characterised in that at least one component of the spatial orientation of the fibres (2) is identified as the angle s formed by the fibres (2) relative to the first polarisation plane (pS), also being characterised in that the angle s is calculated with the formula:

$$s = k * a * \frac{(i1 - i2) - (i1 - i3)}{(i1 - i2) + (i1 - i3)}$$

where k is an arithmetic constant, a is the absolute value of the angle formed by the lateral planes relative to the central plane, i1 is the intensity of the light detected according to the central reference plane, i2 is the intensity of the light detected according to a first lateral reference plane and i3 is the intensity of the light detected according to the other lateral reference plane.

7. The method according to claim 1, characterised in that the second polarisation plane (pX2) of the reflected light (5) is identified as a combination of the intensities of said components.

8. The method according to claim 7, characterised in that the step of detecting the intensity of the components of the reflected light (5) involves observation of the illuminated zone according to a predetermined direction of observation (7) and detection of first components of the reflected light (5) according to a plurality of separate reference polarisation planes (P1), (P2), (P3), (P4) belonging to a bundle and identifying a shared straight line (8) which has its own predetermined direction of extension.

9. The method according to claim 8, characterised in that the step of detecting the reflected light (5) is repeated while observing the illuminated zone according to a plurality of predetermined directions of observation (7) to identify a plurality of additional spatial components of the orientation of the fibres (2), also being characterised in that the spatial orientation of the fibres (2) is identified as a combination of said plurality of components.

10. The method according to claim 8, characterised in that the first components are detected according to the three reference polarisation planes (P1), (P2), (P3), said three planes being one central plane and two lateral planes rotated relative to the central plane through an angle of rotation which is identical in opposite directions, the absolute value of the angle between the central plane and the lateral planes being selected between 10° and 45° and in that the central reference plane is selected so that it coincides with the first polarisation plane (pS).

11. The method according to claim 10, characterised in that at least one component of the spatial orientation of the fibres (2) is identified as the angle s formed by the fibres (2) relative to the first polarisation plane (pS), also being characterised in that the angle s is calculated with the formula:

$$s = k * a * \frac{(i1 - i2) - (i1 - i3)}{(i1 - i2) + (i1 - i3)}$$

where k is an arithmetic constant, a is the absolute value of the angle formed by the lateral planes relative to the central plane, i1 is the intensity of the light detected according to the central reference plane, i2 is the intensity of the light detected according to a first lateral reference plane and i3 is the intensity of the light detected according to the other lateral reference plane.

12. The method according to claim 1, characterised in that the first polarisation plane (pS) is selected so that it is parallel to a nominal orientation of the fibres (2) of the piece of wood (3).

13. The method according to claim 1, characterised in that the operating steps are carried out for a plurality of separate beams of light which illuminate different zones of the surface of the wood (3).

14. The method according to claim 1, characterised in that it also involves the operating step of feeding the piece of wood (3) along a feed trajectory T and also being characterised in that the other steps are repeated for a plurality of illuminated zones positioned one after another along the piece of wood (3).

15. The method according to claim 14, characterised in that the beams of light are coplanar and together form on said surface an overall illuminated zone with a linear extension (9) and in that the overall illuminated zone is generated across the feed trajectory T so that it covers the entire width of the piece of wood (3) transversally to the feed trajectory T.

16. The method according to claim 1, wherein said detecting step includes detecting the intensity of components of the reflected light (5) with respect to a fourth separate reference polarisation plane (P4).

17. An apparatus for identifying the orientation of fibres (2) in a piece of wood (3) comprising:
means for supporting a piece of wood (3) to be examined;
a light source (10) for generating at least one beam of light (4) polarised in a first polarisation plane (pS) and, in practice, projecting said beam towards the piece of wood (3) supported by the supporting means;
a detection device (6) in turn comprising at least a first detector (11) facing towards the supporting means for detecting, according to its own direction of observation (7), the light coming from a zone of the piece of wood (3) illuminated by the beam of light (4) after reflection of the beam of light (4) on the piece of wood (3), and means (12) for filtering, based on its polarisation, the light detected by the first detector (11); and
a processing device operatively connected at least to the detection device (6) for processing what is detected and identifying the orientation of the wood fibres (2) at the illuminated zone;
the apparatus being characterised in that the filtering means (12) comprise a plurality of polarised filters (13) designed to filter the light coming from the illuminated zone of the piece of wood (3), according to at least three separate reference polarisation planes (P1), (P2), (P3), and also being characterised in that the first detector (11) comprises means for detecting the intensity of the light in each of the at least three reference polarisation planes (P1), (P2), (P3).

18. The apparatus according to claim 17, characterised in that the detection device (6) also comprises splitter means (14) for evenly splitting the light detected on the detection means.

19. The apparatus according to claim 18, characterised in that the splitter means (14) comprise a prismatic refractor (16) for the beam of light with a plurality of operating portions (17), their number being equal to the number of reference polarisation planes (P1), (P2), (P3), each of the portions causing a different deflection of a beam of light passing through it.

20. The apparatus according to claim 18, characterised in that the splitter means (14) comprise a prismatic refractor (16) for the beam of light with a plurality of operating portions (17), their number being a multiple of the number of reference polarisation planes (P1), (P2), (P3), (P4), identical operating portions (17) being grouped together, the number of groups of identical operating portions (17) being equal to the number of reference polarisation planes (P1), (P2), (P3), (P4), and each operating portion of a group causing a deflection of a beam of light passing through it which is identical to those of the other portions of the same group and different to that of the operating portions (17) of the other groups.

21. The apparatus according to claim 17, characterised in that the polarised filters (13) are positioned upstream or downstream of splitter means (14) with reference to the direction of propagation of the light towards the first detector (11).

* * * * *